US008812841B2

(12) United States Patent
Sievert et al.

(10) Patent No.: US 8,812,841 B2
(45) Date of Patent: Aug. 19, 2014

(54) COMMUNICATIONS HUB FOR USE IN LIFE CRITICAL NETWORK

(75) Inventors: James Sievert, Shoreview, MN (US);
Eric P. Bailey, Roseville, MN (US);
William Mass, Renton, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 407 days.

(21) Appl. No.: 12/694,817

(22) Filed: Jan. 27, 2010

(65) Prior Publication Data

US 2010/0228977 A1 Sep. 9, 2010

Related U.S. Application Data

(60) Provisional application No. 61/157,455, filed on Mar. 4, 2009.

(51) Int. Cl.
*H04L 29/06* (2006.01)
*H04L 9/32* (2006.01)
*G08B 1/08* (2006.01)
*A61N 1/00* (2006.01)

(52) U.S. Cl.
USPC ......... 713/168; 713/153; 340/539.12; 607/31

(58) Field of Classification Search
USPC .......... 713/150–153, 168–169, 172; 709/240; 607/31; 340/539.12
See application file for complete search history.

(56) References Cited

U.S. PATENT DOCUMENTS

| 4,211,235 A | 7/1980 | Keller et al. |
|---|---|---|
| 5,012,411 A | 4/1991 | Policastro et al. |
| 5,033,286 A | 7/1991 | Guardiani |
| 5,047,930 A | 9/1991 | Martens et al. |
| 5,113,869 A | 5/1992 | Nappholz et al. |
| 5,293,642 A | 3/1994 | Lo |
| 5,336,245 A | 8/1994 | Adams et al. |
| 5,339,824 A | 8/1994 | Engira |

(Continued)

FOREIGN PATENT DOCUMENTS

| EP | 1681803 | 7/2006 |
|---|---|---|
| JP | 08329374 | 12/1996 |

(Continued)

OTHER PUBLICATIONS

Biotronic Technical Manual for Philos DR-T, DDDR Dual Chamber Pulse Generator with Home Monitor, 2004, 32 pages.

(Continued)

*Primary Examiner* — Darren B Schwartz
(74) *Attorney, Agent, or Firm* — Pauly, DeVries Smith & Deffner, LLC

(57) ABSTRACT

Secured communications between patient portable communicators (PPC) and a central authority (CA) via an unsecured network are implemented using software implemented by a communications device. The communications device provides for detecting, using a multiplicity of disparate communication protocols, presence of entities requesting a network connection and determining whether or not each of the entities is a PPC, establishing, only for the entities determined to be PPCs, a connection to the CA via the unsecured network using the disparate communication protocols, authenticating only the PPCs to the CA, and facilitating communication of PPC data between the PPCs and the CA via the communications device and the unsecured network upon successful PPC authentication. The PPC data comprises at least some patient implantable medical device data acquired by the PPCs.

18 Claims, 19 Drawing Sheets

(56) References Cited

U.S. PATENT DOCUMENTS

| | | |
|---|---|---|
| 5,383,915 A | 1/1995 | Adams |
| 5,400,246 A | 3/1995 | Wilson et al. |
| 5,438,983 A | 8/1995 | Falcone |
| 5,462,051 A | 10/1995 | Oka et al. |
| 5,464,012 A | 11/1995 | Falcone |
| 5,465,082 A | 11/1995 | Chaco |
| 5,522,396 A | 6/1996 | Langer et al. |
| 5,579,775 A | 12/1996 | Dempsey et al. |
| 5,620,472 A | 4/1997 | Rahbari |
| 5,634,468 A | 6/1997 | Platt et al. |
| 5,674,249 A | 10/1997 | de Coriolis et al. |
| 5,720,770 A | 2/1998 | Nappholz |
| 5,720,771 A | 2/1998 | Snell |
| 5,749,907 A | 5/1998 | Mann |
| 5,752,976 A | 5/1998 | Duffin et al. |
| 5,759,199 A | 6/1998 | Snell |
| 5,827,180 A | 10/1998 | Goodman |
| 5,867,821 A * | 2/1999 | Ballantyne et al. ............... 705/2 |
| 5,873,040 A | 2/1999 | Dunn et al. |
| 5,880,867 A | 3/1999 | Mahany |
| 5,891,178 A | 4/1999 | Mann et al. |
| 5,899,855 A | 5/1999 | Brown |
| 5,904,708 A | 5/1999 | Goedeke |
| 5,959,529 A | 9/1999 | Kail et al. |
| 6,050,940 A | 4/2000 | Braun et al. |
| 6,083,248 A | 7/2000 | Thompson |
| 6,088,594 A | 7/2000 | Kingdon et al. |
| 6,093,146 A | 7/2000 | Filangeri |
| 6,095,985 A | 8/2000 | Raymond et al. |
| 6,161,095 A | 12/2000 | Brown |
| 6,221,011 B1 | 4/2001 | Bardy |
| 6,225,901 B1 | 5/2001 | Kail, IV |
| 6,270,457 B1 | 8/2001 | Bardy |
| 6,277,072 B1 | 8/2001 | Bardy |
| 6,280,380 B1 | 8/2001 | Bardy |
| 6,282,441 B1 | 8/2001 | Raymond et al. |
| 6,287,252 B1 | 9/2001 | Lugo |
| 6,292,687 B1 | 9/2001 | Lowell et al. |
| 6,312,378 B1 | 11/2001 | Bardy |
| 6,325,756 B1 | 12/2001 | Webb et al. |
| 6,330,426 B2 | 12/2001 | Brown et al. |
| 6,336,903 B1 | 1/2002 | Bardy |
| 6,353,761 B1 | 3/2002 | Conley et al. |
| 6,358,203 B2 | 3/2002 | Bardy |
| 6,363,282 B1 | 3/2002 | Nichols et al. |
| 6,368,284 B1 | 4/2002 | Bardy |
| 6,377,843 B1 | 4/2002 | Naydenov et al. |
| 6,396,416 B1 | 5/2002 | Kuusela et al. |
| 6,398,727 B1 | 6/2002 | Bui et al. |
| 6,398,728 B1 | 6/2002 | Bardy |
| 6,402,691 B1 | 6/2002 | Peddicord et al. |
| 6,405,083 B1 | 6/2002 | Rockwell et al. |
| 6,406,426 B1 | 6/2002 | Reuss et al. |
| 6,411,840 B1 | 6/2002 | Bardy |
| 6,413,213 B1 | 7/2002 | Essenpreis et al. |
| 6,418,346 B1 | 7/2002 | Nelson et al. |
| 6,428,475 B1 | 8/2002 | Shen |
| 6,434,429 B1 | 8/2002 | Kraus et al. |
| 6,440,066 B1 | 8/2002 | Bardy |
| 6,442,432 B2 | 8/2002 | Lee |
| 6,450,953 B1 | 9/2002 | Place et al. |
| 6,453,200 B1 | 9/2002 | Koslar |
| 6,456,256 B1 | 9/2002 | Amundson et al. |
| 6,466,819 B1 | 10/2002 | Weiss |
| 6,470,215 B1 | 10/2002 | Kraus et al. |
| 6,477,363 B1 | 11/2002 | Ayoub et al. |
| 6,477,424 B1 | 11/2002 | Thompson et al. |
| 6,480,745 B2 | 11/2002 | Nelson et al. |
| 6,485,418 B2 | 11/2002 | Yasushi et al. |
| 6,497,655 B1 | 12/2002 | Linberg et al. |
| 6,512,944 B1 | 1/2003 | Kovtun et al. |
| 6,544,171 B2 | 4/2003 | Beetz et al. |
| 6,544,173 B2 | 4/2003 | West et al. |
| 6,553,262 B1 | 4/2003 | Lang et al. |
| 6,556,871 B2 | 4/2003 | Schmitt et al. |
| 6,558,320 B1 | 5/2003 | Causey, III et al. |
| 6,564,104 B2 | 5/2003 | Nelson et al. |
| 6,564,108 B1 | 5/2003 | Makar et al. |
| 6,569,095 B2 | 5/2003 | Eggers |
| 6,574,509 B1 | 6/2003 | Kraus et al. |
| 6,574,510 B2 | 6/2003 | Von Arx et al. |
| 6,574,742 B1 | 6/2003 | Jamroga et al. |
| 6,577,899 B2 | 6/2003 | Lebel et al. |
| 6,584,356 B2 | 6/2003 | Wassmund et al. |
| 6,591,242 B1 | 7/2003 | Karp et al. |
| 6,599,250 B2 | 7/2003 | Webb et al. |
| 6,602,191 B2 | 8/2003 | Quy |
| 6,609,023 B1 | 8/2003 | Fischell et al. |
| 6,609,115 B1 | 8/2003 | Mehring |
| 6,611,206 B2 | 8/2003 | Eshelman et al. |
| 6,614,406 B2 | 9/2003 | Amundson et al. |
| 6,622,043 B1 | 9/2003 | Kraus et al. |
| 6,622,044 B2 | 9/2003 | Bange et al. |
| 6,622,050 B2 | 9/2003 | Thompson |
| 6,650,939 B2 | 11/2003 | Taepke, II et al. |
| 6,664,893 B1 | 12/2003 | Eveland et al. |
| 6,665,385 B2 | 12/2003 | Rogers et al. |
| 6,665,565 B1 | 12/2003 | Stomberg et al. |
| 6,675,045 B2 | 1/2004 | Mass et al. |
| 6,694,177 B2 | 2/2004 | Eggers et al. |
| 6,701,183 B2 | 3/2004 | Baker et al. |
| 6,708,065 B2 | 3/2004 | Von Arx et al. |
| 6,712,762 B1 | 3/2004 | Lichter et al. |
| 6,720,887 B1 | 4/2004 | Zunti |
| D490,525 S | 5/2004 | Stein et al. |
| 6,731,311 B2 | 5/2004 | Bufe et al. |
| 6,735,479 B2 | 5/2004 | Fabian et al. |
| 6,735,551 B2 | 5/2004 | Voegeli et al. |
| 6,749,566 B2 | 6/2004 | Russ |
| 6,758,812 B2 | 7/2004 | Lang |
| 6,763,269 B2 | 7/2004 | Cox |
| 6,766,201 B2 | 7/2004 | Von Arx et al. |
| 6,773,396 B2 | 8/2004 | Flach et al. |
| 6,783,492 B2 | 8/2004 | Dominguez et al. |
| 6,785,573 B2 | 8/2004 | Kovtun et al. |
| 6,792,321 B2 | 9/2004 | Sepe, Jr. |
| 6,801,137 B2 | 10/2004 | Eggers |
| 6,801,802 B2 | 10/2004 | Sitzman et al. |
| 6,804,557 B1 | 10/2004 | Kroll |
| 6,804,558 B2 | 10/2004 | Haller et al. |
| 6,804,559 B1 | 10/2004 | Kraus et al. |
| 6,809,701 B2 | 10/2004 | Amundson et al. |
| 6,820,057 B1 | 11/2004 | Loch et al. |
| 6,840,904 B2 | 1/2005 | Goldberg |
| 6,850,252 B1 | 2/2005 | Hoffberg |
| 6,878,112 B2 | 4/2005 | Linberg et al. |
| 6,885,288 B2 | 4/2005 | Pincus |
| 6,889,086 B2 | 5/2005 | Mass et al. |
| 6,893,395 B1 | 5/2005 | Kraus et al. |
| 6,903,657 B2 | 6/2005 | Kwoen |
| 6,915,265 B1 | 7/2005 | Johnson |
| 6,936,007 B2 | 8/2005 | Quy |
| 6,940,403 B2 | 9/2005 | Kail, IV |
| 6,941,168 B2 | 9/2005 | Girouard |
| 6,954,673 B2 | 10/2005 | Von Arx et al. |
| 6,957,102 B2 | 10/2005 | Silver et al. |
| 6,957,107 B2 | 10/2005 | Rogers et al. |
| 6,958,705 B2 | 10/2005 | Lebel |
| 6,961,621 B2 | 11/2005 | Krishnan et al. |
| 6,963,907 B1 | 11/2005 | McBride et al. |
| 6,970,737 B1 | 11/2005 | Brodnick et al. |
| 6,976,958 B2 | 12/2005 | Quy |
| 6,978,169 B1 | 12/2005 | Guerra |
| 6,978,182 B2 | 12/2005 | Mazar et al. |
| 6,980,112 B2 | 12/2005 | Nee |
| 6,985,771 B2 | 1/2006 | Fischell et al. |
| 6,988,989 B2 | 1/2006 | Weiner et al. |
| 6,993,393 B2 | 1/2006 | Von Arx et al. |
| 7,002,468 B2 | 2/2006 | Eveland et al. |
| 7,009,511 B2 | 3/2006 | Mazar et al. |
| 7,016,739 B2 | 3/2006 | Bange et al. |
| 7,043,305 B2 | 5/2006 | KenKnight et al. |
| 7,058,453 B2 | 6/2006 | Nelson et al. |
| 7,060,030 B2 | 6/2006 | Von Arx et al. |

(56) References Cited

U.S. PATENT DOCUMENTS

| | | |
|---|---|---|
| 7,065,409 B2 | 6/2006 | Mazar |
| 7,066,883 B2 | 6/2006 | Schmidt et al. |
| 7,070,562 B2 | 7/2006 | Bardy et al. |
| 7,072,718 B2 | 7/2006 | Von Arx et al. |
| 7,079,035 B2 | 7/2006 | Bock et al. |
| 7,096,067 B2 | 8/2006 | Linberg |
| 7,096,068 B2 | 8/2006 | Mass et al. |
| 7,099,715 B2 | 8/2006 | Korzinov et al. |
| 7,104,955 B2 | 9/2006 | Bardy et al. |
| 7,117,031 B2 | 10/2006 | Lohman et al. |
| 7,120,488 B2 | 10/2006 | Nova et al. |
| 7,123,950 B2 | 10/2006 | Mannheimer |
| 7,130,396 B2 | 10/2006 | Rogers et al. |
| 7,134,996 B2 | 11/2006 | Bardy et al. |
| 7,149,570 B2 | 12/2006 | Ellscheid et al. |
| 7,149,773 B2 | 12/2006 | Haller et al. |
| 7,151,435 B2 | 12/2006 | Brackett et al. |
| 7,155,290 B2 | 12/2006 | Von Arx et al. |
| 7,156,808 B2 | 1/2007 | Quy |
| 7,156,809 B2 | 1/2007 | Quy |
| 7,181,017 B1 | 2/2007 | Nagel |
| 7,181,505 B2 | 2/2007 | Haller et al. |
| 7,194,300 B2 | 3/2007 | Korzinov |
| 7,203,545 B2 | 4/2007 | Schmitt et al. |
| 7,204,378 B2 | 4/2007 | Schaeff |
| 7,209,790 B2 | 4/2007 | Thompson et al. |
| 7,212,849 B2 | 5/2007 | Zhang et al. |
| 7,212,850 B2 | 5/2007 | Prystowsky |
| 7,218,969 B2 | 5/2007 | Vallapureddy et al. |
| 7,240,833 B2 | 7/2007 | Zarembo |
| 7,257,447 B2 | 8/2007 | Cates et al. |
| 7,270,633 B1 | 9/2007 | Goscha |
| 7,273,454 B2 | 9/2007 | Raymond et al. |
| 7,283,864 B2 | 10/2007 | Thomas et al. |
| 7,286,872 B2 | 10/2007 | Kramer et al. |
| 7,289,761 B2 | 10/2007 | Mazar |
| 7,292,139 B2 | 11/2007 | Mazar et al. |
| 7,313,441 B2 | 12/2007 | Mass et al. |
| 7,316,648 B2 | 1/2008 | Kelly et al. |
| 7,319,903 B2 | 1/2008 | Bange et al. |
| 7,324,850 B2 | 1/2008 | Persen et al. |
| 7,353,063 B2 | 4/2008 | Simms, Jr. |
| 7,359,753 B2 | 4/2008 | Bange et al. |
| 7,363,080 B2 | 4/2008 | Stubbs et al. |
| 7,373,200 B2 | 5/2008 | Stubbs et al. |
| 7,378,955 B2 | 5/2008 | Mazar et al. |
| 7,383,087 B2 | 6/2008 | Hoyme et al. |
| 7,383,088 B2 | 6/2008 | Spinelli et al. |
| 7,389,146 B2 | 6/2008 | Hanson et al. |
| 7,392,086 B2 | 6/2008 | Sathaye |
| 7,392,092 B2 | 6/2008 | Li et al. |
| 7,395,117 B2 | 7/2008 | Mazar et al. |
| 7,536,557 B2 | 5/2009 | Murakami et al. |
| 7,751,801 B2 | 7/2010 | Torvinen |
| 7,752,059 B2 | 7/2010 | Sweeney |
| 7,830,381 B2 | 11/2010 | Lundstrom et al. |
| 7,978,062 B2 | 7/2011 | LaLonde et al. |
| 8,373,556 B2 | 2/2013 | Lalonde et al. |
| 2001/0051787 A1* | 12/2001 | Haller et al. .................. 604/66 |
| 2002/0010679 A1 | 1/2002 | Felsher |
| 2002/0052539 A1 | 5/2002 | Haller |
| 2002/0055917 A1 | 5/2002 | Muraca |
| 2002/0082480 A1 | 6/2002 | Riff |
| 2003/0025602 A1 | 2/2003 | Medema et al. |
| 2003/0088290 A1* | 5/2003 | Spinelli et al. ................ 607/30 |
| 2003/0227414 A1 | 12/2003 | Saliga |
| 2004/0006265 A1 | 1/2004 | Alhussiny |
| 2004/0048601 A1* | 3/2004 | Lee et al. .................... 455/410 |
| 2004/0117308 A1 | 6/2004 | Bouknight |
| 2004/0122488 A1* | 6/2004 | Mazar et al. ................. 607/60 |
| 2004/0128161 A1 | 7/2004 | Mazar et al. |
| 2004/0170154 A1 | 9/2004 | Carter et al. |
| 2004/0176811 A1 | 9/2004 | Von Arx et al. |
| 2004/0230246 A1 | 11/2004 | Stein et al. |
| 2004/0230247 A1 | 11/2004 | Stein et al. |
| 2004/0233930 A1 | 11/2004 | Colby, Jr. |
| 2004/0260189 A1 | 12/2004 | Eggers et al. |
| 2005/0021370 A1 | 1/2005 | Riff |
| 2005/0027329 A1 | 2/2005 | Holmquist et al. |
| 2005/0032511 A1 | 2/2005 | Malone et al. |
| 2005/0071199 A1* | 3/2005 | Riff .................................. 705/3 |
| 2005/0091338 A1 | 4/2005 | De la Huerga |
| 2005/0113900 A1 | 5/2005 | Shiroff et al. |
| 2005/0114711 A1 | 5/2005 | Hesselink |
| 2005/0120082 A1 | 6/2005 | Hesselink |
| 2005/0124866 A1* | 6/2005 | Elaz et al. ..................... 600/301 |
| 2005/0125258 A1 | 6/2005 | Yellin |
| 2005/0131479 A1 | 6/2005 | Axelrod et al. |
| 2005/0144186 A1 | 6/2005 | Hesselink |
| 2005/0144195 A1 | 6/2005 | Hesselink |
| 2005/0144200 A1 | 6/2005 | Hesselink |
| 2005/0149481 A1 | 7/2005 | Hesselink |
| 2005/0159105 A1 | 7/2005 | Mass et al. |
| 2005/0160147 A1 | 7/2005 | Denny et al. |
| 2005/0192649 A1 | 9/2005 | Shehadeh et al. |
| 2005/0192836 A1 | 9/2005 | Rossinni et al. |
| 2005/0192837 A1 | 9/2005 | Fears et al. |
| 2005/0192838 A1 | 9/2005 | Jones et al. |
| 2005/0206518 A1* | 9/2005 | Welch et al. ............. 340/539.12 |
| 2005/0241026 A1 | 10/2005 | Esler et al. |
| 2005/0245995 A1 | 11/2005 | Diebold |
| 2005/0251227 A1 | 11/2005 | Khoo et al. |
| 2005/0282494 A1 | 12/2005 | Kossi |
| 2005/0288808 A1 | 12/2005 | Lopez et al. |
| 2006/0020314 A1 | 1/2006 | Bodner |
| 2006/0020960 A1 | 1/2006 | Relan |
| 2006/0030810 A1 | 2/2006 | Mandrusov et al. |
| 2006/0047318 A1 | 3/2006 | Pastore et al. |
| 2006/0052084 A1 | 3/2006 | Diebold et al. |
| 2006/0064133 A1 | 3/2006 | Von Arx et al. |
| 2006/0064142 A1 | 3/2006 | Chavan et al. |
| 2006/0064143 A1 | 3/2006 | Von Arx et al. |
| 2006/0074465 A1* | 4/2006 | Webb .............................. 607/60 |
| 2006/0089856 A1 | 4/2006 | Kadhiresan et al. |
| 2006/0106433 A1 | 5/2006 | Mazar et al. |
| 2006/0111759 A1 | 5/2006 | Hoyme et al. |
| 2006/0116744 A1 | 6/2006 | Von Arx et al. |
| 2006/0122667 A1 | 6/2006 | Chavan et al. |
| 2006/0133362 A1 | 6/2006 | Stein et al. |
| 2006/0136717 A1* | 6/2006 | Buer et al. .................... 713/155 |
| 2006/0139229 A1 | 6/2006 | Theobold et al. |
| 2006/0142820 A1 | 6/2006 | Von Arx et al. |
| 2006/0142821 A1 | 6/2006 | Bange et al. |
| 2006/0154642 A1 | 7/2006 | Scannell, Jr. |
| 2006/0159074 A1 | 7/2006 | Diebold et al. |
| 2006/0161213 A1 | 7/2006 | Patel |
| 2006/0161223 A1 | 7/2006 | Vallapureddy et al. |
| 2006/0173985 A1 | 8/2006 | Moore |
| 2006/0194615 A1 | 8/2006 | Vallapureddy et al. |
| 2006/0195162 A1 | 8/2006 | Von Arx et al. |
| 2006/0195163 A1 | 8/2006 | KenKnight et al. |
| 2006/0200007 A1 | 9/2006 | Brockway et al. |
| 2006/0206246 A1 | 9/2006 | Walker |
| 2006/0218054 A1 | 9/2006 | Postelnik et al. |
| 2006/0220839 A1* | 10/2006 | Fifolt et al. ............. 340/539.12 |
| 2006/0241712 A1 | 10/2006 | Cates et al. |
| 2006/0253158 A1 | 11/2006 | Stubbs et al. |
| 2006/0253163 A1 | 11/2006 | Stubbs et al. |
| 2006/0253300 A1 | 11/2006 | Somberg et al. |
| 2006/0253301 A1 | 11/2006 | Simms et al. |
| 2006/0253894 A1 | 11/2006 | Bookman |
| 2006/0265740 A1 | 11/2006 | Clark |
| 2007/0018810 A1 | 1/2007 | Smythe et al. |
| 2007/0027723 A1 | 2/2007 | Bardy |
| 2007/0036771 A1 | 2/2007 | Wagner et al. |
| 2007/0049983 A1 | 3/2007 | Freeberg |
| 2007/0049992 A1 | 3/2007 | Freeberg |
| 2007/0053516 A1 | 3/2007 | Katoozi et al. |
| 2007/0061266 A1 | 3/2007 | Moore |
| 2007/0078491 A1 | 4/2007 | Siejko et al. |
| 2007/0083246 A1 | 4/2007 | Mazar et al. |
| 2007/0100384 A1 | 5/2007 | Fischell et al. |
| 2007/0100396 A1 | 5/2007 | Freeberg |
| 2007/0100397 A1 | 5/2007 | Seeberger et al. |

(56) References Cited

U.S. PATENT DOCUMENTS

| | | |
|---|---|---|
| 2007/0106129 A1 | 5/2007 | Srivathsa et al. |
| 2007/0106536 A1 | 5/2007 | Moore |
| 2007/0106537 A1 | 5/2007 | Moore |
| 2007/0106750 A1 | 5/2007 | Moore |
| 2007/0106751 A1 | 5/2007 | Moore |
| 2007/0106752 A1 | 5/2007 | Moore |
| 2007/0106753 A1 | 5/2007 | Moore |
| 2007/0106754 A1 | 5/2007 | Moore |
| 2007/0116036 A1 | 5/2007 | Moore |
| 2007/0116037 A1 | 5/2007 | Moore |
| 2007/0118188 A1 | 5/2007 | Von Arx et al. |
| 2007/0123943 A1 | 5/2007 | Patangay et al. |
| 2007/0123946 A1 | 5/2007 | Masoud |
| 2007/0129642 A1 | 6/2007 | Korzinov |
| 2007/0130657 A1 | 6/2007 | Rogers et al. |
| 2007/0135855 A1 | 6/2007 | Foshee et al. |
| 2007/0135865 A1 | 6/2007 | Schmitt et al. |
| 2007/0136098 A1 | 6/2007 | Smythe et al. |
| 2007/0138253 A1 | 6/2007 | Libin |
| 2007/0142727 A1 | 6/2007 | Zhang et al. |
| 2007/0150010 A1 | 6/2007 | Stubbs et al. |
| 2007/0150028 A1 | 6/2007 | Parkinson et al. |
| 2007/0156054 A1 | 7/2007 | Korzinov et al. |
| 2007/0157298 A1 | 7/2007 | Dingwall |
| 2007/0168222 A1 | 7/2007 | Hoyme et al. |
| 2007/0168461 A1 | 7/2007 | Moore |
| 2007/0175827 A1 | 8/2007 | Wariar |
| 2007/0179349 A1 | 8/2007 | Hoyme et al. |
| 2007/0180047 A1 | 8/2007 | Dong et al. |
| 2007/0185547 A1 | 8/2007 | Hoyme et al. |
| 2007/0185550 A1 | 8/2007 | Vallapureddy et al. |
| 2007/0191723 A1 | 8/2007 | Prystowsky et al. |
| 2007/0192140 A1 | 8/2007 | Gropper |
| 2007/0195163 A1 | 8/2007 | Chestak et al. |
| 2007/0203754 A1 | 8/2007 | Harrington |
| 2007/0206615 A1 | 9/2007 | Plamondon et al. |
| 2007/0210923 A1 | 9/2007 | Butler |
| 2007/0226013 A1 | 9/2007 | Elletson et al. |
| 2007/0251835 A1* | 11/2007 | Mehta et al. ............... 205/783 |
| 2007/0260293 A1 | 11/2007 | Carpenter et al. |
| 2007/0263873 A1 | 11/2007 | Qi et al. |
| 2007/0265533 A1 | 11/2007 | Tran |
| 2007/0273504 A1 | 11/2007 | Tran |
| 2007/0276270 A1 | 11/2007 | Tran |
| 2007/0282634 A1 | 12/2007 | Johnson et al. |
| 2007/0288067 A1 | 12/2007 | Eveland |
| 2007/0288069 A1 | 12/2007 | Goscha et al. |
| 2007/0293776 A1 | 12/2007 | Korzinov et al. |
| 2007/0299317 A1 | 12/2007 | Hoyme et al. |
| 2008/0001735 A1 | 1/2008 | Tran |
| 2008/0004904 A1 | 1/2008 | Tran |
| 2008/0015655 A1 | 1/2008 | Bange et al. |
| 2008/0015656 A1 | 1/2008 | Bange et al. |
| 2008/0021521 A1 | 1/2008 | Shah et al. |
| 2008/0021523 A1 | 1/2008 | Cates et al. |
| 2008/0021524 A1 | 1/2008 | Goscha et al. |
| 2008/0021730 A1 | 1/2008 | Holla |
| 2008/0021741 A1 | 1/2008 | Holla |
| 2008/0021834 A1 | 1/2008 | Holla |
| 2008/0024294 A1* | 1/2008 | Mazar ..................... 340/539.12 |
| 2008/0027499 A1 | 1/2008 | Srivathsa et al. |
| 2008/0040151 A1 | 2/2008 | Moore |
| 2008/0055070 A1 | 3/2008 | Bange et al. |
| 2008/0058651 A1 | 3/2008 | Shen et al. |
| 2008/0058881 A1 | 3/2008 | Wagner et al. |
| 2008/0061961 A1 | 3/2008 | John |
| 2008/0071183 A1 | 3/2008 | Thomas et al. |
| 2008/0071314 A1 | 3/2008 | John |
| 2008/0086185 A1 | 4/2008 | Amurthur et al. |
| 2008/0103542 A1 | 5/2008 | Hoyme et al. |
| 2008/0109051 A1 | 5/2008 | Splinter et al. |
| 2008/0114412 A1 | 5/2008 | Bange et al. |
| 2008/0140163 A1 | 6/2008 | Keacher |
| 2008/0154099 A1 | 6/2008 | Aspel |
| 2008/0157928 A1 | 7/2008 | Butler |
| 2008/0164975 A1 | 7/2008 | Butler |
| 2008/0164977 A1 | 7/2008 | Butler |
| 2008/0177194 A1 | 7/2008 | Zhang et al. |
| 2008/0180249 A1 | 7/2008 | Butler |
| 2008/0186137 A1 | 8/2008 | Butler |
| 2008/0186138 A1 | 8/2008 | Butler |
| 2008/0186139 A1 | 8/2008 | Butler |
| 2008/0186180 A1 | 8/2008 | Butler |
| 2008/0209513 A1* | 8/2008 | Graves et al. ..................... 726/2 |
| 2008/0211630 A1 | 9/2008 | Butler |
| 2008/0222711 A1 | 9/2008 | Michaelis |
| 2008/0252459 A1 | 10/2008 | Butler |
| 2008/0294019 A1 | 11/2008 | Tran |
| 2008/0306872 A1 | 12/2008 | Felsher |
| 2009/0019552 A1 | 1/2009 | McLaughlin |
| 2009/0024178 A1* | 1/2009 | Hennig ........................... 607/30 |
| 2009/0024416 A1 | 1/2009 | McLaughlin |
| 2009/0058635 A1 | 3/2009 | LaLonde et al. |
| 2009/0058636 A1 | 3/2009 | Gaskill et al. |
| 2009/0062887 A1 | 3/2009 | Mass et al. |
| 2009/0063187 A1 | 3/2009 | Johnson et al. |
| 2009/0063193 A1 | 3/2009 | Barton et al. |
| 2009/0099866 A1* | 4/2009 | Newman ........................... 705/2 |
| 2009/0146822 A1* | 6/2009 | Soliman ..................... 340/573.1 |
| 2009/0158274 A1* | 6/2009 | Roberts ........................ 717/178 |
| 2009/0222898 A1 | 9/2009 | Veidung |
| 2009/0231125 A1* | 9/2009 | Baldus et al. ............. 340/539.12 |
| 2009/0240526 A1* | 9/2009 | Vesto et al. ..................... 705/3 |
| 2009/0320029 A1 | 12/2009 | Kottomtharayil |
| 2010/0144316 A1* | 6/2010 | Piercy et al. ................... 455/411 |
| 2010/0225468 A1 | 9/2010 | Sievert et al. |
| 2010/0228977 A1 | 9/2010 | Sievert et al. |
| 2011/0202371 A1* | 8/2011 | Darguesse et al. ................ 705/3 |
| 2012/0068847 A1* | 3/2012 | Pirzada ..................... 340/573.1 |
| 2013/0076535 A1 | 3/2013 | Sievert et al. |
| 2013/0133011 A1 | 5/2013 | Chhaochharia et al. |
| 2013/0147622 A1 | 6/2013 | LaLonde et al. |
| 2013/0154851 A1 | 6/2013 | Gaskill et al. |
| 2013/0262311 A1 | 10/2013 | Buhrmann et al. |
| 2013/0310896 A1 | 11/2013 | Mass |
| 2014/0111353 A1 | 4/2014 | Sievert et al. |

FOREIGN PATENT DOCUMENTS

| | | |
|---|---|---|
| JP | 2003047599 | 2/2003 |
| JP | 2005080175 | 3/2005 |
| JP | 2007200276 | 8/2007 |
| WO | WO 97/36443 | 10/1997 |
| WO | WO03077994 | 9/2003 |
| WO | WO 03/100647 | 12/2003 |
| WO | WO 2004/109992 | 12/2004 |
| WO | WO2006010166 | 1/2006 |
| WO | WO2009032134 | 3/2009 |

OTHER PUBLICATIONS

Medtronic Analyzer Reference Guide for Medtronic Carelink Analyzer, Model 2290 Analyzer for Medtronic and Vitatron Devices, 2008, 106 pages.

Medtronic Programmer Reference Guide for Medtronic Carelink Programmer, Model 2090 Programmer for Medtronic and Vitatron Devices, 2008, 112 pages.

International Search Report and Written Opinion dated Apr. 9, 2009 from International Application No. PCT/US2008/010162, 24 pages.

International Preliminary Report on Patentability dated Mar. 1, 2010 from International Application No. PCT/US2008/010162, 13 pages.

U.S. Appl. No. 12/694,826, filed Jan. 27, 2010, Sievert et al.

Invitation to Pay Additional Fees dated Jul. 12, 2010 from PCT Application No. PCT/US2010/026076, 6 pages.

Savci et al., "MICS Transceivers: Regulatory Standards and Applications", IEEE Proceedings, Apr. 8, 2005. pp. 179-182.

Valdastri et al., "An implantable ZigBee ready telemetric platform for in vivo monitoring of physiological parameters," Sensors and Actuators A, vol. 142, 2008, pp. 369-378.

Office Action dated Oct. 5, 2010 from U.S. Appl. No. 12/151,869, 6 pages.

Office Action Response submitted Oct. 7, 2010 to office action dated Oct. 5, 2010 from U.S. Appl. No. 12/151,869, 9 pages.

(56) References Cited

OTHER PUBLICATIONS

International Search Report and Written Opinion from International Application No. PCT/US2010/026076 dated Oct. 11, 2010, 17 pages.
Office Action Response dated Sep. 4, 2012 for U.S. Appl. No. 12/151,910, 13 pages.
Notice of Allowance dated Sep. 10, 2012 for U.S. Appl. No. 13/181,176, 7 pages.
Margolis et al., Latitude Active Monitoring alerts physician of silent AF episode, Latitude Patient Management Case Study, Boston Scientific Corporation, 2006, 2 pages.
JP Office Action with translation dated Mar. 28, 2012 from JP Application No. 2010-522944, 4 pages.
File History for U.S. Appl. No. 12/151,869.
File History for U.S. Appl. No. 12/228,915.
File History for European Application No. 08795636.3 as retrieved from the European Patent Office Electronic Filing System on Jun. 15, 2012, 92 pages.
File History for U.S. Appl. No. 12/151,910.
File History for U.S. Appl. No. 12/151,780.
File History for U.S. Appl. No. 12/151,796.
File History for U.S. Appl. No. 13/181,176.
File History for U.S. Appl. No. 12/694,826.
Klemm, Fabius et al., "Alleviating effects of mobility on TCP performance in ad hoc networks using signal strength based link management", Lecture notes in Computer Science, vol. 2775, 2003, pp. 611-624.
"File History for co-owned, U.S. Appl. No. 13/758,489", Entitled "Medical Data Transport Over Wireless Life Critical Network,", filed Feb. 4, 2013 (325 pages).
"File History for co-owned, U.S. Appl. No. 12/151,796", Entitled "Dashboard Diagnostics for Wireless Patient Communicator,", filed May 9, 2008 (604 pages).
"File History for co-owned, co-pending U.S. Appl. No. 13/684,893", Entitled "Modular Patient Communicator for Use in Life Critical Network,", filed Nov. 26, 2012 (237 pages).
"JP Office Action Translation", for Japanese Application No. 2011553082, mailed Dec. 18, 2012 (14 pages).
"File History for U.S. Appl. No. 14/071,893", 276 pages.
"Partial File History for U.S. Appl. No. 12/228,915", 182 pages.
Final Office Action, for U.S. Appl. No. 12/228,915, mailed May 28, 2014 (40 pages).
"Final Office Action", for U.S. Appl. No. 14/071,893, mailed Mar. 13, 2014 (9 pages).
"Notice of Allowance", for U.S. Appl. No. 13/955,746, mailed Apr. 22, 2014 (49 pages).

* cited by examiner

COMMUNICATIONS HUB FOR USE IN LIFE CRITICAL NETWORK

RELATED APPLICATIONS

This application claims the benefit of Provisional Patent Application Ser. No. 61/157,455, filed on Mar. 4, 2009, to which priority is claimed pursuant to 35 U.S.C. §119(e) and which is hereby incorporated herein by reference, and is related to Provisional Patent Application Ser. Nos. 60/967,060, 60/967,061, 60/967,062, and 60/967,063 respectively filed on Aug. 31, 2007; 61/128,583, filed on May 22, 2008; and 61/157,451, filed on Mar. 4, 2009; and to Non-Provisional U.S. patent application Ser. No. 12/151,869, issued Jul. 12, 2011 as U.S. Pat. No. 7,978,062, U.S. patent application Ser. No. 12/151,780, issued Aug. 20, 2013 as U.S. Pat. No. 8,515,547, U.S. patent application Ser. No. 12/151,910, issued Mar. 12, 2013 as U.S. Pat. No. 8,395,498, U.S. patent application Ser. No. 12/151,796, filed on May 9, 2008; and 12/228,915 filed on Aug. 18, 2008; and all of which are hereby incorporated herein by reference in their entireties.

FIELD OF THE INVENTION

The present invention relates generally to systems, devices, and methods for transporting medical information over a network.

BACKGROUND

Implantable pulse generators (IPGs) are medical devices commonly used to treat irregular heartbeats, known as arrhythmias. Cardiac pacemakers, for example, are designed to manage bradycardia, an abnormally slow or irregular heartbeat. Left untreated, bradycardia can cause symptoms such as fatigue, dizziness, and fainting. Cardiac resynchronizers are a particular class of pacemaker that provide cardiac resynchronization therapy, such a bi-ventricular pacing, for patients suffering from heart failure. Implantable cardioverter defibrillators (ICDs), by way of further example, are designed to treat tachycardia, heart rhythms that are abnormally fast and life threatening. Some forms of tachycardia can result in sudden cardiac death, if left untreated.

Implantable pulse generators are increasingly being equipped with an on-board, volatile memory in which telemetered signals can be stored for later retrieval and analysis. The telemetered signals provide various types of patient device information, such as atrial electrical activity, ventricular electrical activity, time of day, activity level, cardiac output, and any interventions made on a per heartbeat or binned average basis. In addition, a growing class of cardiac medical devices, including implantable heart failure monitors, implantable event monitors, cardiovascular monitors, and therapy devices, are being used to provide similar stored device information. Telemetered signals are also stored in a broader class of monitors and therapeutic devices for other areas of medicine, including metabolism, endocrinology, hematology, neurology, muscular, gastrointestinal, genitalurology, ocular, auditory, and the like.

Information stored in an implantable medical device is typically retrieved using a proprietary interrogator or programmer, often during a clinic visit or following a device event. The volume of data retrieved from a single device interrogation procedure can be large and proper interpretation and analysis can require significant physician time and detailed subspecialty knowledge, particularly by cardiologists and cardiac electrophysiologists. Present approaches to data interpretation and understanding, and practical limitations on time and physician availability, make such analyses impracticable.

Conventional systems for collecting and analyzing pacemaker and ICD telemetered signals in a clinical or office setting can be used to retrieve data, such as patient electrocardiogram and any measured physiological signals, collected by the IPG for recordation, display and printing. The retrieved data may be displayed in chronological order and analyzed by a physician. Conventional systems often lack remote communications facilities and must be operated with the patient present. These systems present a limited analysis of the collected data based on a single device.

SUMMARY OF THE INVENTION

The present invention is generally directed to systems, devices, methods, and software that provide for transportation of medical information over a network. In particular, the present invention is directed to systems, devices, methods, and software that provide for secured communications between a multiplicity of portable patient communicators and a central authority over an unsecured network. Embodiments of the invention are directed to hubs, switches, routers, medical device programmers, and other communication devices that can be implemented to facilitate secured transport of patient implantable medical device data between a multiplicity of portable patient communicators and a central authority over an unsecured network.

In accordance with embodiments of the present invention, a communications device is configured to facilitate secured communications between a multiplicity of PPCs and a CA. Each of the PPCs is configured to effect connectivity with a PIMD in accordance with medical firmware or software program instructions implemented by the processor of the PPC. The communications device includes a housing, a logical network port provided at the housing and adapted to facilitate communications between the device and the unsecured network, and a multiplicity of logical local ports provided at the housing and adapted to implement a plurality of disparate communication protocols for effecting connectivity between the device and the plurality of PPCs.

A processor of the device is coupled to the logical network port and the logical local ports. A memory is coupled to the processor and configured to store life critical network software. The LCN software comprises program instructions which, when executed by the processor, cause the processor to determine whether or not entities requesting a network connection via the device are PPCs, authenticate only PPCs to the CA, facilitate communication between the PPCs and the CA via the logical local ports, the logical network port, and the unsecured network upon successful PPC authentication, and transfer PPC data to the CA. At least some of the PPC data comprises PIMD data.

Methods, according to embodiments of the present invention, provide for secured communications between a multiplicity of PPCs and a CA using a communications device via an unsecured network. Method embodiments involve detecting, using a multiplicity of disparate communication protocols implemented by the communications device, presence of each of a plurality of entities requesting a network connection and determining whether or not each of the entities is a PPC. Method embodiments involve establishing, only for the entities determined to be PPCs, a connection to the CA via the unsecured network using the disparate communication protocols implemented by the communications device, authenticating only the PPCs to the CA via the communications device and the unsecured network, and facilitating communication of PPC data between the PPCs and the CA via the communications device and the unsecured network upon successful PPC authentication. The PPC data comprises at least some PIMD data acquired from PIMDs by their respective PPCs.

According to various embodiments of the present invention, a computer-readable medium has instructions stored thereon which are executable by a data processing arrangement disposed in a communications device and capable of being coupled to an unsecured network. Program instructions stored on the computer-readable medium facilitate processor implementation of detecting, using a multiplicity of disparate communication protocols implemented by the communications device, presence of each of a plurality of entities requesting a network connection, determining whether or not each of the entities is a PPC, establishing, only for the entities determined to be PPCs, a connection to the CA via the unsecured network using the disparate communication protocols implementable by the communications device, authenticating only the PPCs to the CA via the communications device and the unsecured network, and facilitating communication of PPC data between the PPCs and the CA via the communications device and the unsecured network upon successful PPC authentication. The PPC data comprises at least some PIMD data acquired from PIMDs by their respective PPCs.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
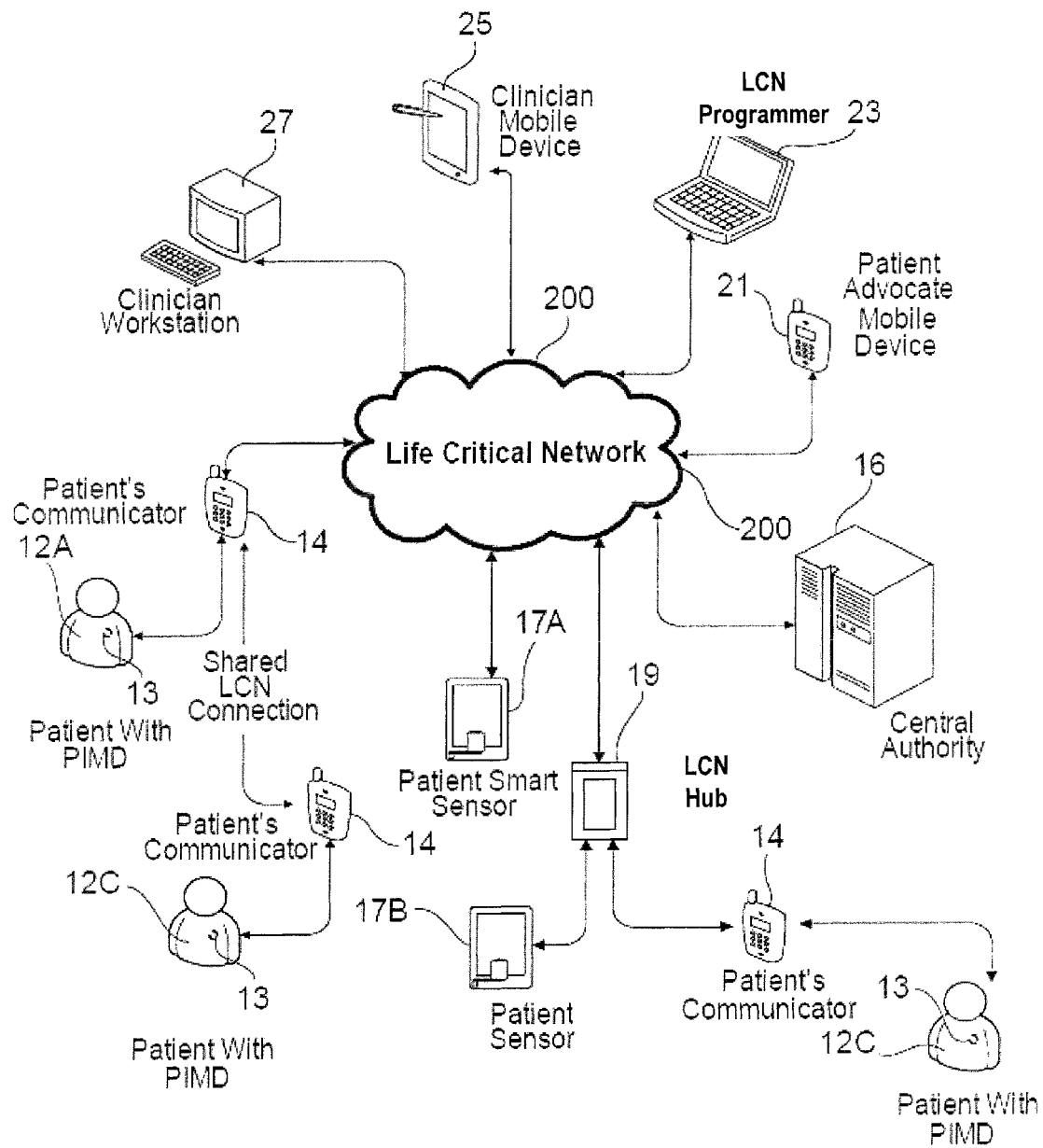
FIG. 1A is a system diagram of a life critical network (LCN) implementation in accordance with embodiments of the present invention.
Figure 1B:
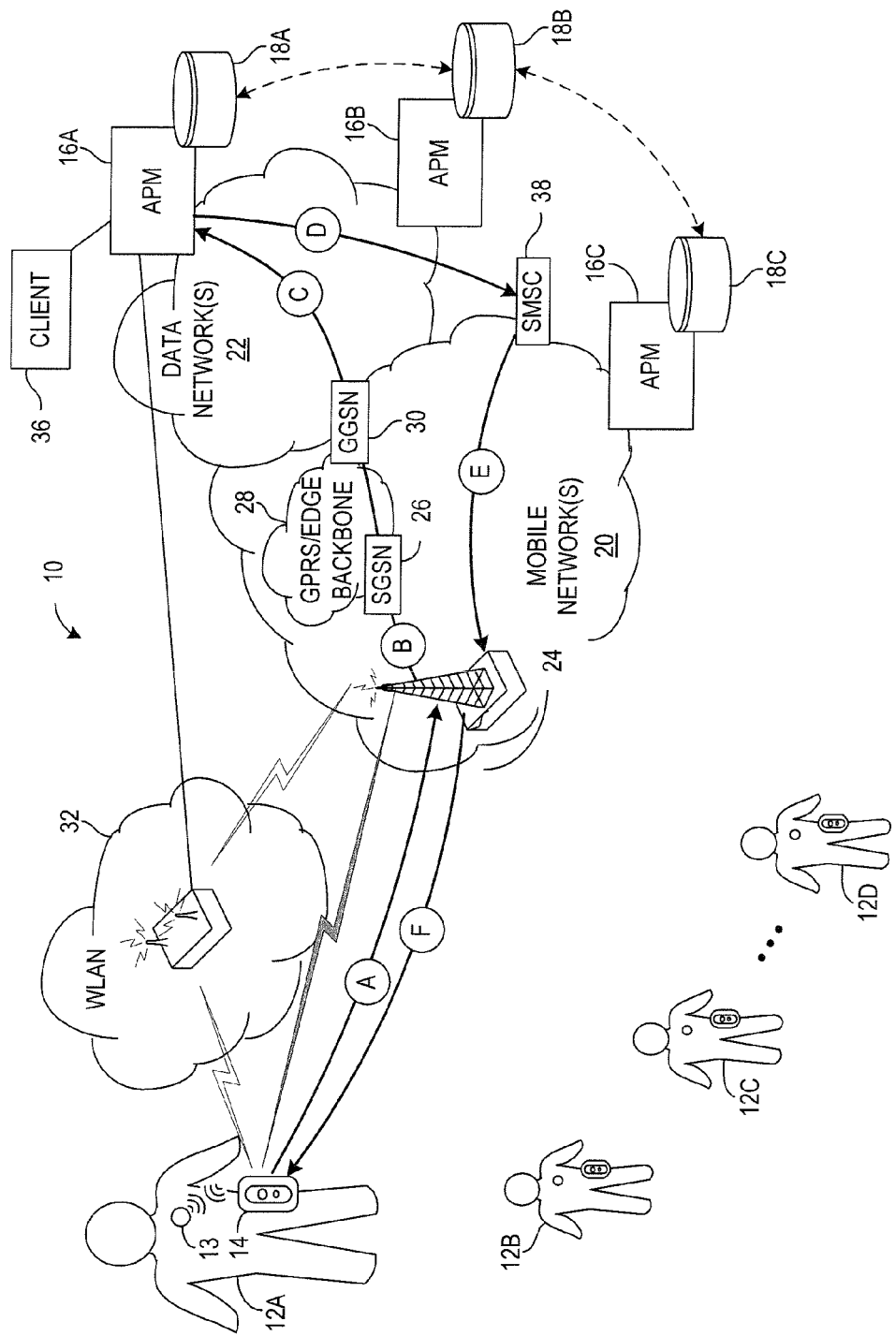
FIG. 1B illustrates an exemplary automated or advanced patient management or monitoring (APM) server system environment supported within an LCN in accordance with embodiments of the present invention.
Figure 2A:
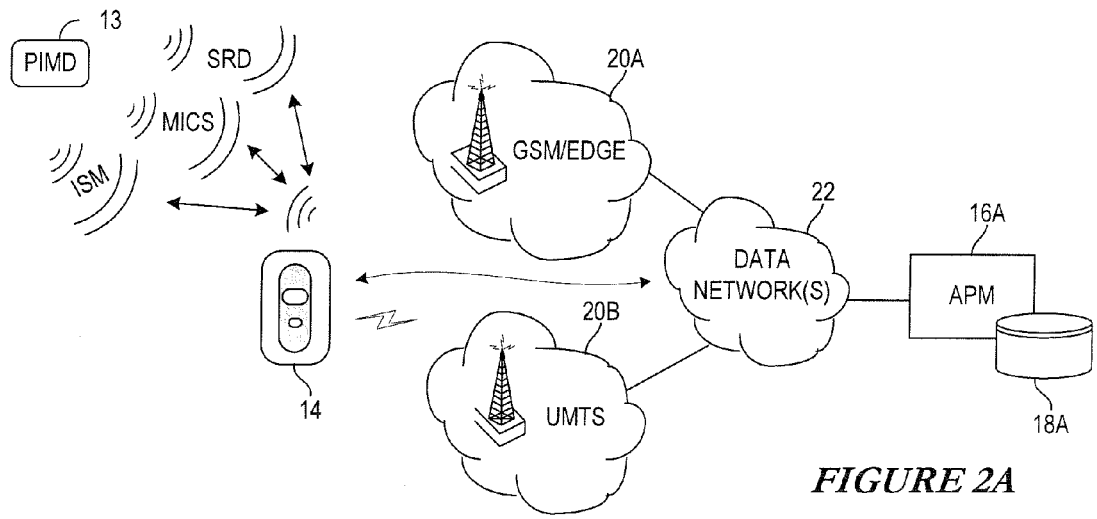
FIG. 2A illustrates a patient implantable medical device configured to operate in various frequency bands or channels for communicating with a portable patient communicator in the context of a LCN in accordance with embodiments of the present invention.
Figure 2B:
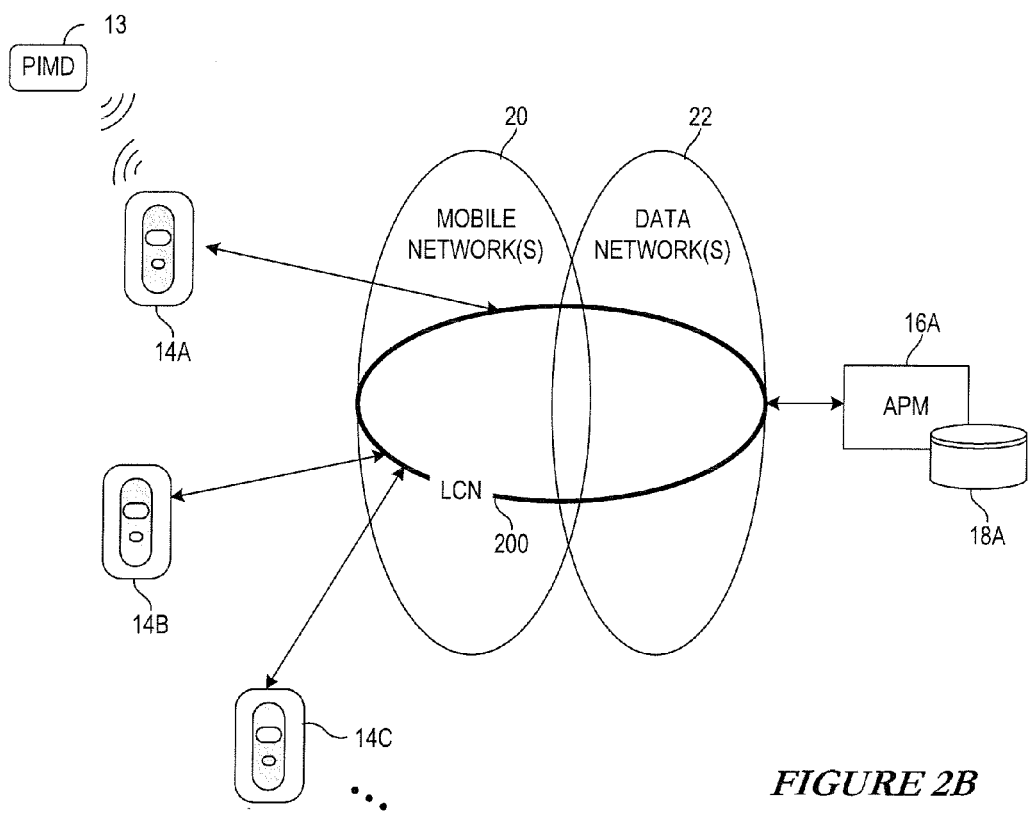
FIG. 2B illustrates a multiplicity of portable patient communicators (PPC) that communicate implantable medical device data to a central authority (e.g., APM server or system) via an LCN comprising one or more of mobile and data networks in accordance with embodiments of the present invention.
Figure 3:
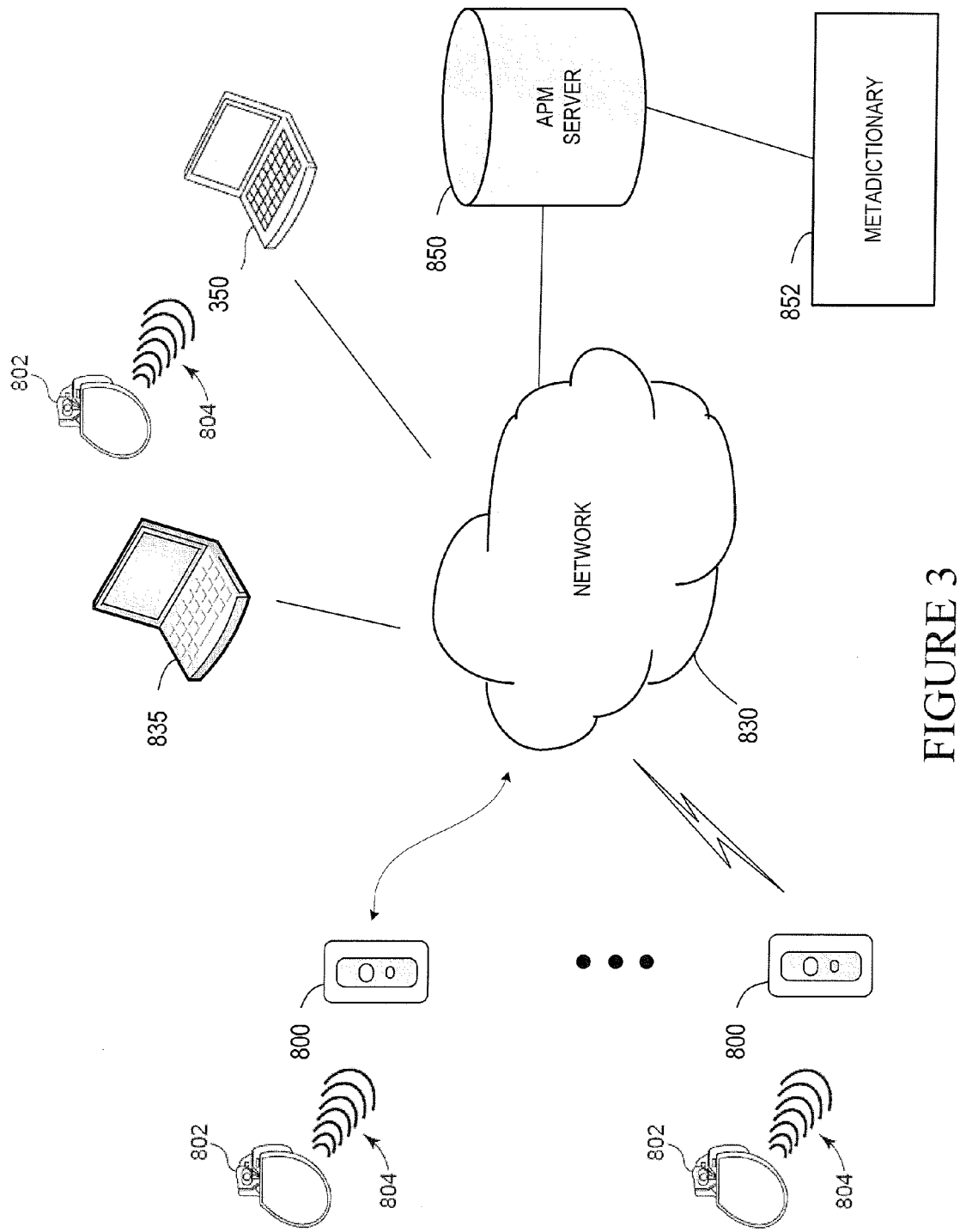
FIG. 3 shows an illustration of a multiplicity of PPCs communicatively coupled to an APM server via an LCN network connection in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein. For example, a device or system may be implemented to include one or more of the advantageous features and/or processes described below. It is intended that such a device or system need not include all of the features described herein, but may be implemented to include selected features that provide for useful structures, systems, and/or functionality.

A life critical network as described herein is preferably configured as a robust network supported by existing mobile and data networks, and exhibiting heightened communication attributes such as guaranteed delivery, high quality of service (QoS), and tight security. A life critical network implemented in accordance with this disclosure provides for the acquisition of physiologic and contextual data acquired for any number of patients that are each carrying a portable communications device, referred to herein as a portable patient communicator.

Acquisition of physiologic data by a central authority of the life critical network for individual patients may advantageously occur on an unscheduled basis, such as in response to predefined events (e.g., tachycardia events) or in response to patient initiated interrogations. In this regard, a life critical network may acquire patient data for any number of patients that carry a PPC on an event-driven basis, in contrast to a time-scheduled basis.

Patient physiologic data may be acquired by the CA while the patient is ambulatory, such as during daily routines at the home or office, or when traveling locally, nationally or worldwide. Physiologic data for patients may be acquired by a wide variety of sensors, including external and internal sensors. For example, a patient implantable medical device (PIMD), such as a pacemaker or ICD, may acquire physiologic data and transmit such data to the PPC.

Data acquired by the PPC may be transmitted to a CA of the life critical network in real-time, such as by use of a real-time data streaming protocol. Store-and-forward data transfer protocols may also be employed, such as for less critical data or when a real-time data transfer connection is not available. Incremental data transfers may also be performed to reduce the volume of data transferred from the PPC to the CA. A life critical network of the present invention provides connectivity between a patient's PPC and CA that can be dynamically adjusted to meet the needs of the patient, physician, emergency services, and system/technical personnel.

Real-time transfer of patient physiologic data may be triggered by real-time clinical events detected by a sensor or implantable medical device provided with the patient. Data transfers may also be triggered in accordance with query/response protocols. Clinical alerts for high risk patients may be communicated through the life critical network in real-time. Physiologic monitoring for remote triage may be implemented in real-time through the life critical network.

Examples of patient data that may be transferred from the PPC to the CA include electrograms (EGMs), clinical event data, episode counters, alerts, device or sensor settings, battery status, lead measurements, and patient activity level, among other types of data. Data transferred from the PPC to the CA may be integrated at a web site supported by the CA and displayed at a remote location (e.g., physician's office).

Although technically feasible, large scale implementation of an LCN that facilitates network connectivity between a CA and a vast number of PPCs may be hampered by economic considerations, such as costs associated with system/device deployment and communications, as well as uncertainty in governmental reimbursement for such investments. For example, there is increasing pressure to reduce the expense of PPCs and long-term communication costs, particularly the relatively high cost of cellular connectivity.

There is an increasing desire to increase LCN connectivity options afforded PPCs. Certain environments lend themselves to supporting the goals of reduced PPC cost while increasing LCN connectivity. Also, connectivity of a programmer to an LCN has been desired for some time. LCN connectivity can provide an authorized programmer with the ability to obtain software updates and upload initial patient data via an LCN/CA connection, among other capabilities.

Embodiments of the present invention are directed to a communication hub that provides an interface to an LCN for a multiplicity of PPCs that communicate with the hub via a multiplicity of communication protocols. According to various embodiments, an LCN hub of the present invention is a physical device that provides LCN access to PPCs. It is to be understood that the term "hub" as used herein is intended to cover a range of communication devices, including repeaters, switches, and routers, among others. In many embodiment descriptions, the term hub is used interchangeably with such other communications devices.

In this regard, an LCN hub of the present invention is distinguishable from an ordinary network hub, switch or router in that the LCN hub provides LCN access only to PPCs, programmers, or other approved/authorized LCN devices. An LCN hub of the present invention preferably provides varied forms of PPC connectivity to an LCN, such as through both diversified WAN and diversified local LAN ports. An LCN hub of the present invention advantageously permits use of existing network resources in order to effectively extend the LCN to remote and typically ambulatory patients provided with a PPC.

Embodiments of the present invention are directed to a medical device programmer implemented to communicate with a CA via an LCN. Embodiments of an LCN programmer may, in general, be similar to conventional programmers. Unlike a conventional programmer that operates either as a stand-alone system or connects with a private secured network/sever, an LCN programmer of the present invention is itself an entity that connects to the LCN via unsecured networks (e.g., the Internet) and can further be implemented to act as an LCN hub. An LCN programmer can act as a data collection facility for PPCs.

For example, an LCN programmer may be stationed in a hospital ER or in the waiting room of a clinic, and can triage implantable medical device patients as they enter the door of the facility. For example, an LCN programmer stationed at an ER entrance can detect presence of the patient's PPC, automatically interrogate the PPC, authenticate and connect the PPC with the LCN, and upload data acquired from the PPC/implanted medical device to a CA via the LCN.

A secured LCN provider preferably prevents entities other than approved entities from gaining access to the LCN. In the context of an Internet-based implementation, a secured provider will not provide an LCN IP address to any entity other than for example, a PPC, LCN hub, an LCN programmer, or a generic hub or switch that is provided with and executes authorized LCN operating and security software, thereby operating as a secured LCN hub or switch.

For example, an LCN hub or programmer, when equipped with 802.11, Bluetooth, or USB via a local logical port, can use any number of authentication protocols to allow PPC access to the LCN. One such protocol is 802.1X or Extensible Authentication Protocol (EAP). The specific EAP authentication method is one of many possible methods, and includes pre-shared keys and a Remote Authentication Dial In User Service (RADIUS) network protocol. Authentication is provided through contact with the CA, located on the LCN.

An LCN hub of the present invention allows medical device manufacturers, clinics, and physicians to leverage existing network infrastructures in order to provide LCN access to a vast number of PPCs associated with a vast number of patients. Advantages afforded embodiments of the present invention include reductions in patient/medical device data transmission costs. This is especially pertinent in high-density environments such as nursing homes. Reductions in the cost of PPC manufacturing and deployment are also realizable, due to use of less expensive technologies such as Bluetooth. Enhanced features are provided by embodiments that employ LCN programmers for connecting with a CA, and provides additional benefits for hospitals, clinics, and patients.

Embodiments of the present invention are directed to a modular PPC. A modular PPC typically includes sufficient hardware and software to be able to interrogate an implantable medical device (e.g., IPG or other CRM device). Preferably, a modular PCC of the present invention is implemented to incorporate communications circuitry to communicate with the implantable medical device, but excludes a built-in communications facility that, by itself, can communicate with external devices, systems and networks. In other words, communications between the modular PPC and an external device, system or network can be effected only by physically connecting a communications-enabled module or communications cable/connector to a communications interface socket of the PPC. A modular PPC according to embodiments of the invention is purposefully implemented with a reduced capability for effecting communications that rely on built-in protocols. This reduced communications capability provides advantages of reduced PPC build costs and future-proofing the PPC from communication protocols that can become outmoded or obsolete.

These and other advantages of a modular PPC of the present invention are realized by employment of a "universal" communications port. Preferably, a universal communications port of the modular PPC, such as a USB or FireWire™ port, provides a hardware mechanism to access external devices and systems, including an LCN and CA. The universal nature of the modular PPC's communications port allows the PPC to communicate using a wide variety of wireless and wired protocols, such as Bluetooth, 802.11, WiMax, Cellular, Ethernet, FireWire™, and POTS, among others. The universal communications port of a modular PPC may also receive a communications interface connector of a wide variety of devices, such as memory devices (e.g., a memory stick or thumb drive) and sensors, for example, which can expand the functionality of a PPC.

In some embodiments, a modular PPC may be configured as a "universal" host (e.g., USB host). In other embodiments, a modular PPC may be configured as a "universal" host and a "universal" device (e.g., USB device). For purposes of simplicity, and not of limitation, the term USB (Universal Serial Bus) is used herein to denote a port, interface, socket, device, peripheral, host and the like that is "universal" in terms of connectivity. A typical universal communications port of a modular PPC is configured as a serial bus that facilitates connectivity between the PPC and a wide variety of modules, devices, peripherals, systems, and networks.

A universal communications port of a modular PPC is typically a single standardized interface socket that facilitates plug-and-play capabilities by enabling hot swapping, thereby allowing devices to be connected and disconnected to the PPC without rebooting the PPC processor or turning off the PPC. A universal communications port of a modular PPC typically provides power to low-power consumption devices that are connected to the port, thus eliminating the need for the connecting device to includes its own power supply. A universal communications port of a modular PPC advantageously allows many different devices to be connected to the PPC without requiring manufacturer-specific device drivers to be installed.

As previously discussed, a modular PPC according to various embodiments can operate as both a USB device and USB host. According to some embodiments, a USB-OTG (On-the-Go) protocol may be employed by a modular PPC to provide USB device and host functionality. A USB-OTG protocol (USB 2.0 Specification, promulgated by the USB Implementer Forum) is a standard USB that uses a master/slave architecture. In this context, a USB device (e.g., a PPC) can act as both a protocol master and a protocol slave.

Embodiments of a modular PPC can be implemented as a USB host to manage LCN connectivity options, such as Bluetooth, 802.11, WiMax, Cellular, Ethernet, FireWire™, and POTS, for example. A wide variety of detectable modules equipped with a universal port (e.g., USB interface) can be selectably attached to the universal communications port of the PPC. Examples of such detachable modules include memory sticks, thumb drives, physiologic sensors (temperature, blood pressure, blood gas saturation, heart rate, body fat, weight scale), and other external add-on modules. Alternatively, or in addition, the functionality of certain detachable modules may be implemented internally within the PPC, through selective component PCB population and provision of necessary components on the PPC or external element (e.g., electrodes or IR sensor on the PPC housing).

A PPC according to embodiments of the present invention preferably implements LCN software that enables communications between a patient implantable medical device and a central authority via an unsecured network, such as the Internet. In some embodiments, the PPC effects secured communications with a CA by way of a generic (general purpose) network access device. In other embodiments, the PPC effects secured communications with a CA by way of a special purpose network access device, such as an LCN hub or an LCN programmer (or other authorized communications device/system—generic or non-generic—that implements LCN software).

The PPC preferably implements LCN software that provides secured communications with a PIMD and with the central authority. For example, programming instructions of the LCN software executed by a processor of the PPC facilitates connection of the PPC to an unsecured network, authentication of the PPC to the central authority, and transfer of data between the PPC and the central authority. In this regard, the LCN software allows PPCs to communicate to a secure central authority via a life critical network supported by an unsecured network (e.g., the Internet).

According to other embodiments, a PPC may be configured with software that recognizes a special dongle, such as a USB dongle. A dongle generally refers to a small piece of hardware that detachably connects to a computer via a universal interface (e.g., a USB port). Dongles are often implemented to appear as two-interface security tokens with transient data flow that does not collide with the dongle function and a pull communication that reads security data from the dongle. An important function of a dongle is to authenticate a piece of software. Without the dongle, this software will not execute or only does so in a restricted mode.

A USB dongle, according to embodiments of the invention, stores a unique code in a secure area of the dongle that uniquely identifies the dongle as a "PPC key device." The USB dongle is preferably universal in configuration and protocol, and enables PPC special modes. There may be different versions of the dongle that allow a tier of special features on the PPC as security allows. A USB "programming" dongle may be implemented that enables any number of programming capabilities, such as temporarily deactivating an implanted medical device.

A modular PPC of the present invention provides a number advantages, including providing a medical device manufacturer the ability to customize PPCs based on patient need. A modular PPC of the present allows a medical device manufacture the ability to customize PPCs based on device cost requirements (e.g., bradycardia patients—lower cost vs. tachycardia patients—higher cost). A modular PPC of the present provides a medical device manufacture the ability to rapidly adopt new network/server connectivity options as future technologies become available/prevalent.

Embodiments of the invention are directed to systems that are configured to incorporate combinations of PPCs (e.g., modular and non-modular), LCN hubs, and LCN programmers. Some embodiments may include, for example, PPCs and LCN hubs, while others may incorporate PPCs and LCN programmers. Some systems may incorporate LCN hubs and LCN programmers. Other system deployments may incorporate PPCs, LCN hubs, and LCN programmers. These and other combinations of PPCs, LCN hubs, and LCN programmers may be incorporated in systems that include a central authority (e.g., advanced patient management system) and/or LCN infrastructure. It is understood that PPCs, LCN hubs, and LCN programmers are intended to include generic forms of these devices that are modified or upgraded to include appropriate PPC and/or LCN operating system and security software as described herein.

A PPC implemented in accordance with the present invention facilitates acquisition of implantable medical device data and/or patient sensor by a remote system for ambulatory patients. A PPC of the present invention is preferably configured (via internal components or preferably by components of a module connected to a universal port of the PPC) to communicate over existing mobile and/or ground-based data networks, and to effect local wired or wireless communication with one or more internal and/or external physiologic sensors, ambient and/or contextual sensors, implantable medical devices, and/or other external systems or devices.

A PPC of the present invention may be implemented to provide a wide spectrum of capabilities and functionality. For example, the PPC may be configured to provide only a limited number of features, such as in the case of a PPC having a reduced feature set (low-cost configurations). By way of further example, a PPC may be implemented to provide a variety of features and capabilities that enable a wide range of functionality (higher cost configurations).

According to some embodiments, a PPC may provide limited functionality to achieve low cost and future-proofing objectives. For example, a PPC provided with a universal communications port need not be equipped with an internal cellular or other relatively expensive communications device to communicate with an external device, system, or network. Rather, a communications module may be connected to the PPC's universal communications port to effect wired or wireless connectivity with an external device, system, or network.

According to other embodiments, a PPC may be dynamically configurable via interaction with a central authority or an LCN programmer. Dynamically altering the configuration of a PPC serves to enhance cooperative operation between the PPC, implantable medical device/sensor, and the central authority, an embodiment of which is referred to herein as an advanced patient management system or server. Illustrative examples of an APM server system include a remote patient monitoring system and a patient monitoring system that need not be remote relative to the patient's location. Dynamically altering the configuration of a PPC may also serve to conserve power of the implantable medical device or sensor(s) that are communicatively coupled to the PPC.

FIGS. 1A-3 show various implementations of a life critical network in accordance with embodiments of the present invention. The network implementations shown in FIGS. 1A-3 include multiple components linked together to provide a specialized network that guarantees secure and timely delivery of data that are transmitted over one or more networks and attempts to meet specific context sensitive criteria on delivery of that data.

The life critical network 200 essentially provides a private or secured network that is configured to operate on top of existing unsecured mobile and fixed facility networks. The LCN 200 utilizes a secured architecture providing for authentication and management of those components that are allowed access to the network 200. Such components or nodes include, for example, PPCs 14 (modular and non-modular), LCN hubs 19, LCN programmers 23, patient sensors 17A-17B, clinician mobile devices 25, clinician workstations 27, patient advocate mobile devices 21, among others.

The LCN 200 preferably follows cryptographic best practices with regard to confidentiality, integrity, and availability. Given the computational—versus-power requirements, the LCN system 200 can minimize the number of asymmetric cryptographic operations in favor of a symmetric algorithm based on various factors, including a known shared-secret generated or installed at time of manufacture, and a dynamically shifting key based on a seed fed to a pseudo random number generator (e.g., such as model, serial number, and network time).

The LCN system 200 preferably leverages the physical network as a virtualized transport, essentially treating any underlying protocol as potentially unsecured, and thus not relying on any native security mechanisms inherent in any given protocol with regard to the encryption and integrity of its data. The LCN system 200 preferably supports both stateful and stateless connections in order to facilitate asynchronous communication where network bandwidth does not support real-time communication.

The LCN 200, as shown in the embodiment of FIG. 1A, employs a CA (CA) 16 to manage access to the network infrastructure. This typically involves cryptographically validating and authenticating content from a potential node prior to allowing access, and performing other control aspects of policing the network infrastructure. The LCN 200 preferably supports the concept of classification of nodes on the network 200 into a specific hierarchy of access abilities.

The various entities requesting access to the LCN 200 are granted different access rights based on their classification. For example, a low-urgency sensor device 17A-17B or PPC 14 may not be given access to high-speed connectivity if it is classified in a lower urgency or priority tier. A patient implantable medical device programming system 23 may be granted priority access to a higher speed connectivity capability due to its more demanding need for timely interconnection to the infrastructure. This classification and prioritization is preferably dynamically managed via the CA 16. Additional details regarding the LCN implementations shown in FIGS. 1A-3 are provided in several of the references identified herein and incorporated by reference.

Figure 4B:
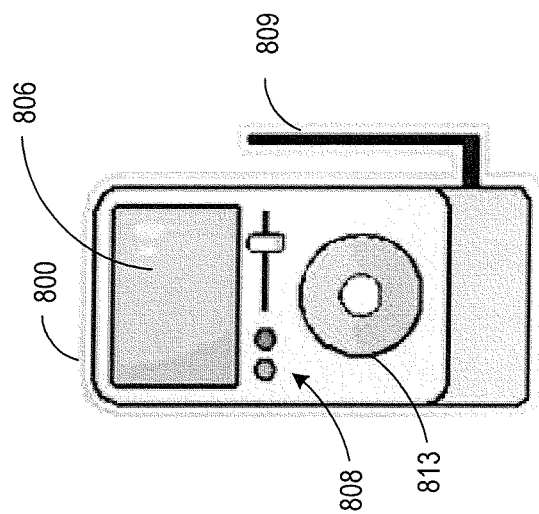
FIG. 4B illustrates a PPC in accordance with other embodiments of the present invention.
Figure 4A:
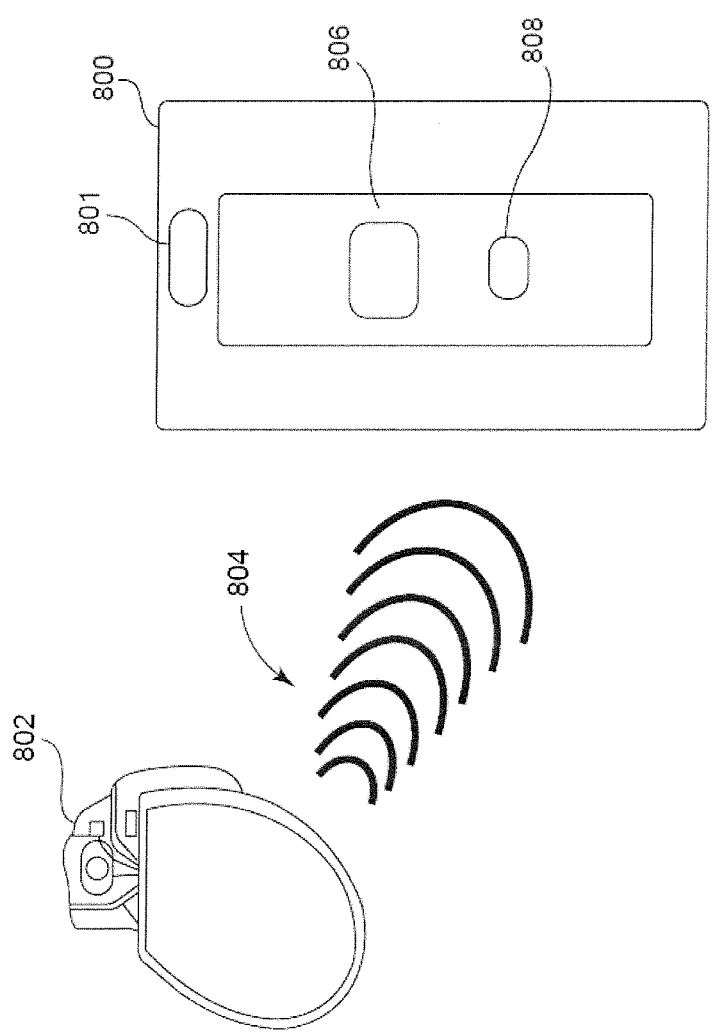
FIG. 4A illustrates a PPC in accordance with embodiments of the present invention.

FIGS. 4A and 4B show different configurations of a PPC 800 in accordance with embodiments of the invention. FIG. 4A shows a PPC 800 communicatively coupled to a patient implantable medical device 802 via a communications link 804. The PPC 800 shown in FIGS. 4A and 4B may be implemented to provide a wide spectrum of capabilities and functionality. Within this spectrum, the PPC 800 may be configured to provide a variety of features or a limited number of features. In some implementations, such as that shown in FIG. 4A, the PPC 800 may be configured to have a reduced number of features and capabilities (e.g., a modular PPC as described hereinbelow in greater detail).

A PPC 800 configured to have a reduced set of features advantageously reduces the complexity and cost of the device, and enhances acceptance of the device by less sophisticated users. A PPC 800 having a reduced set of features also provides for lower power consumption, such as by minimizing or eliminating high power consuming components, such as a color display or other user interface components. The PPC 800 may also be implemented to incorporate a variety of features and capabilities that provide for a wide range of functionality, an example of which is shown in FIG. 4B.

FIG. 4A illustrates a PPC 800 having a reduced feature set and a relatively small form factor. For example, the PPC 800 shown in FIG. 4A may weigh less than about 6 ounces, and be small enough to fit easily in a purse or pocket. The PPC 800 has a simple user interface (U/I), which is shown to include a single button 801, a small LCD 806 that can provide basic status information (e.g., date, time, signal strength, and battery status), and an LED 808. The LED 808 may indicate ON status of the PPC 800 or other operational status indication. In one implementation, illumination of the LED 808 (or illumination of a green color for a multi-color LED 808, for example) may indicate that the PPC's battery is sufficiently charged to provide at least 24 hours (or other duration) of continuous service. The LED 808 may be controlled to implement a flashing scheme, which may include different colors, that communicates information to the patient. For example, a green ON color may indicate acknowledgement that interaction with the user was successful (e.g., a quick flash green light).

The button 801 may provide basic functionality, such as initiating patient-interrogated transmissions and PIMD pairing/re-pairing procedures. The button 801 may also be actuated by the patient for indicating a distress condition of the patient, to which an emergency service may respond (e.g., 911 alert/call). The reduced feature set PPC 800 may exclude a keypad or other more sophisticated user input device. In some configurations, the button 801 may be a multi-functional button (e.g., contact sensitive switch, multi-state switch or rocker switch).

Button activation for controlling PPC functions may include one or more of a quick click, a double click, and a long hold. A button clicking scheme may be developed to perform a variety of operations, including initiating a PIMD 802 interrogation when the patient feels poorly, initiating a connection to the LCN and central authority (e.g., APM server or system), and initiating delivery of a message to pre-determined parties (e.g., physician, neighbors, friends, children, relatives, emergency response service) to alert the recipient that the patient is in distress or need of attention.

A more sophisticated PPC 800 is shown in FIG. 4B. The PPC embodiment shown in FIG. 4B includes an LCD display 806, such as a color OLED. The user interface 801 of the PPC 800 shown in FIG. 4B includes LEDs of different color, a slide switch, and a wheel switch 813 (e.g., touch sensitive/mechanical switch, track-wheel, track pad, etc.). The PPC 800 is shown having a communications wire or cable 809 connected to a universal communications port of the PPC 800, such as an Ethernet, FireWire™, or POTS cable. In some embodiments, the PPCs 800 illustrated in FIGS. 4A and 4B PPC 800 are configured as a modular PPC, which incorporate a universal communications port (e.g., USB) for establishing an LCN connection via a universal cable socket or a detachable module that includes wired or wireless communications circuitry. Such embodiments are directed to "modular" PPCs, representative configurations of which are described hereinbelow.

The PPC 800 shown in FIGS. 4A and 4B may incorporate a speaker (preferably without a microphone in the case of a reduced feature set PPC 800, but a microphone can be included on a more robust PPC configuration). An audible feedback mechanism may be implemented as another means of communicating with the patient. The audible output from the speaker is preferably tonal, but voice output can also be employed. A "quiet mode" can be activated, such as by a 5 second button hold, to disable the speaker and, if desired, transition to a vibration/silent mode, if the PPC 800 is equipped with a vibrator device. The PPC 800 may be programmed to produce tones that can be used to transfer data via a TTM scheme, which can be a backup way of communicating to the central authority if other modes of communication, such as cellular network service, is unavailable.

Figure 5:
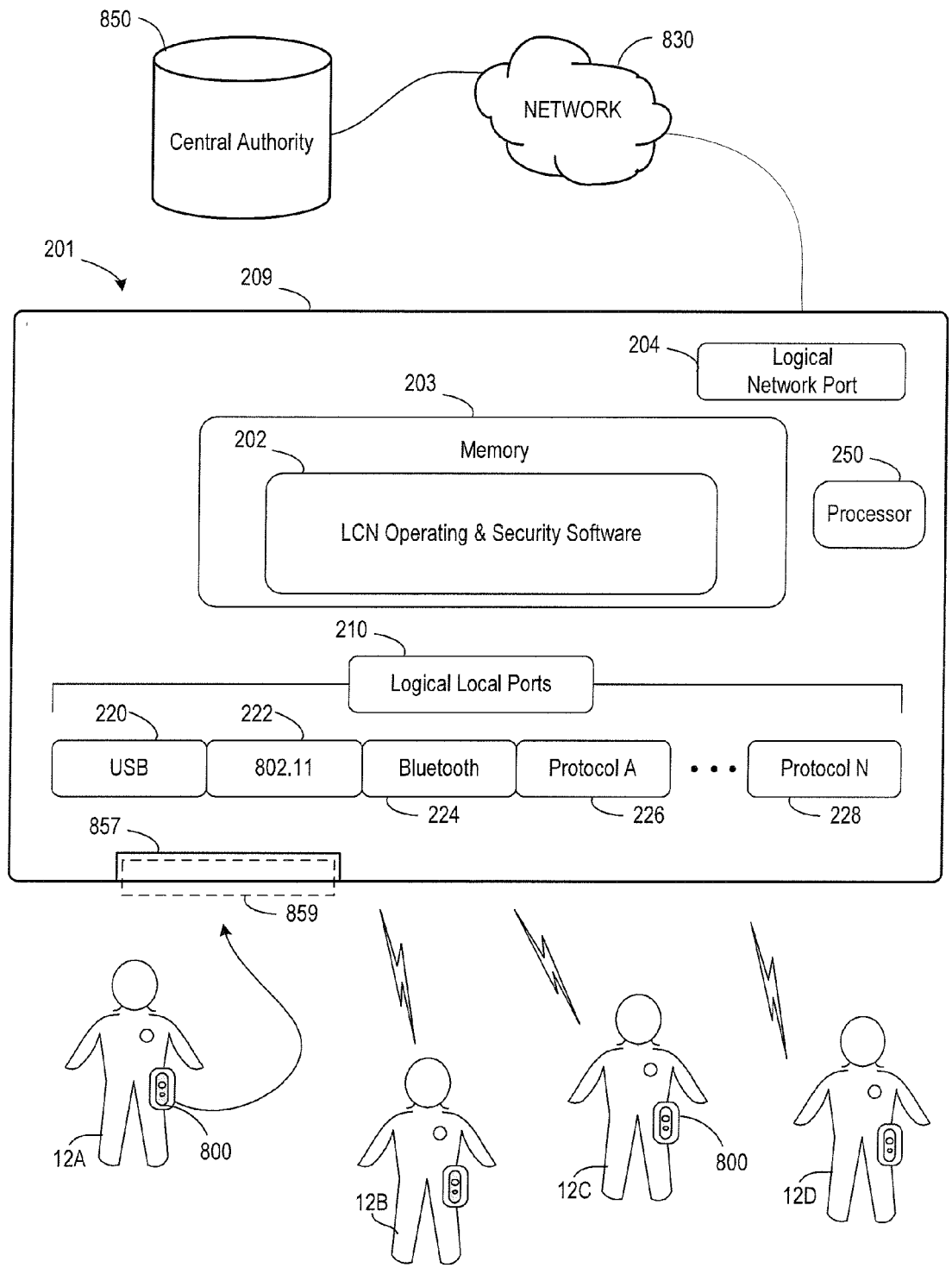
FIG. 5 is an illustration of a communications hub configured to effect communication between a number of PPCs having different communication protocols and a central authority (CA) via an LCN in accordance with embodiments of the present invention.

FIG. 5 is an illustration of a communications hub that effects communication between a number of PPCs having different communication protocols and a central authority via an LCN in accordance with embodiments of the present invention. In the embodiment shown in FIG. 5, a hub 201 is shown communicatively coupled to a CA 850 via a network 830. Preferably, the network 830 is an unsecured network such as the Internet, although some embodiments may involve communication over a semi-secured or secured network.

In general terms, the hub 201 is configured to effect secured communications between a multiplicity of PPCs 800 and the CA 850. The PPCs 800 are adapted to effect connectivity with the CA 850 via an unsecured network 830 (e.g., the Internet) using a multiplicity of disparate communication protocols. The hub 201 includes a housing 209 which houses/supports a number of components. Provided at the housing 209 is a universal communications port 857 which includes a socket configured to receive a properly configured connector or detachable module 859 (depicted as a dashed block for purposes of illustration).

The universal communications port 857 preferably includes a mechanical retention arrangement to provide secured detachable engagement with a properly configured connector or detachable module 859. The universal communications port 857 typically includes contacts that electrically couple to corresponding electrical contacts of the connector or detachable module 859. The universal communications port 857 may alternatively or additionally incorporate an optical communications interface. In addition to signal connectivity provided between the PPC 800 and a detachable module, the universal communications port 857 may also provide power for the detachable module, such as in conformance with a USB port specification.

A logical network port 204 is provided at the housing 209 and adapted to effect communications between the hub 201 and the CA 850 via the unsecured network 830. A multiplicity of logical local ports 210 are provided at the housing 209 and adapted to implement the various disparate communication protocols for effecting connectivity between the hub 201 and the multiplicity of PPCs 800. Memory 203 is provided at the housing and coupled to a processor 205.

The memory 203 is configured to store life critical network software 202 comprising program instructions which, when executed by the processor 250, cause the processor 250 to determine that entities requesting a network connection via the hub 201 are PPCs 800. The processor 250, when executing LCN software 202, authenticates requesting PPCs 800 to the CA 850, and enables communication between the PPCs 800 and CA 850 via the logical local ports 210 and the logical network port 204 upon successful authentication.

The logical local ports 210 facilitate communication between the PPCs 800 and the hub 201 using a variety of different protocols. Preferably, the logical local ports 210 facilitate short-range wireless connectivity between the PPCs 800 and the hub 201, although wired connectivity may be provided. By way of non-limiting example, and as shown in FIG. 5, logical local ports 220 may be configured to implement a USB protocol 220, an IEEE 802 protocol 222, a Bluetooth protocol 224, or other protocol 226-228.

The LCN software 202 resides in memory 203 and comprises program instructions that are executed by processor 250 to perform various tasks, including PPC recognition, establishing network connections, authenticating PPCs 800 to the CA 850, and facilitating data transport between the PPCs 800 and the CA 850 via the logical local ports 210 and logical network port 204, among other tasks. For example, the LCN software 202, when executed by processor 250, provides a connection mapping and authentication to the CA only for entities that are determined by the processor 250 to be PPCs. LCN software 202 executed by the processor 250 preferably effects interrogation of PPCs 800 coming into proximity with the hub 201 and automatic authentication of the PPCs 800 with the CA 850. Execution of the LCN software 202 by the processor 205 preferably effects transfer of PIMD/PCC data to the CA 850 as part of PPC interrogation.

Figure 6:
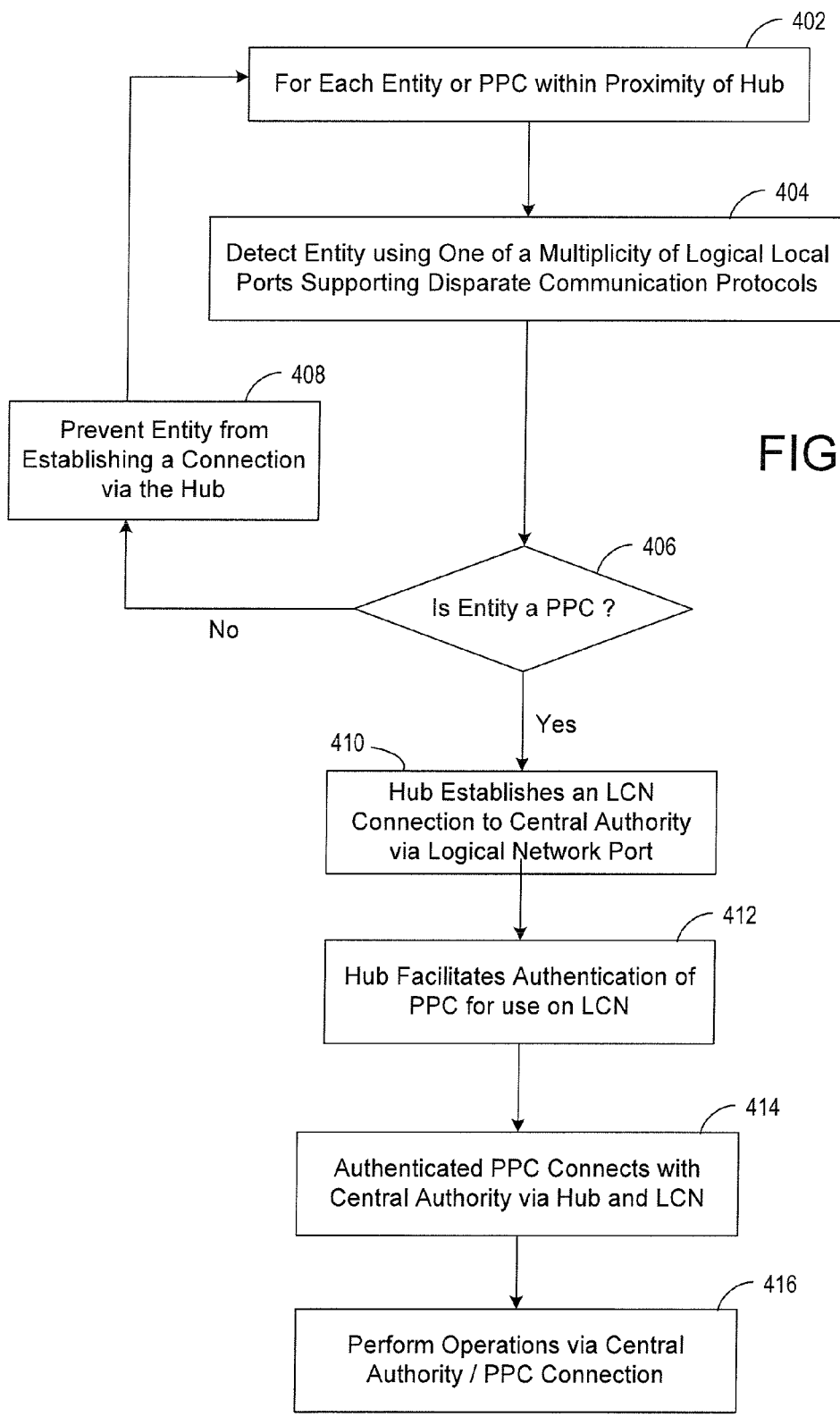
FIG. 6 is a flow chart of various processes for effecting communications for a number of PPCs having different communication protocols with a CA via a communications hub and an LCN in accordance with embodiments of the present invention.

FIG. 6 is a flow chart showing various processes implemented by an LCN hub in accordance with embodiments of the present invention. For each entity or PPC that comes 402 into proximity with the hub, the hub detects 404 presence of the entity or PPC using one of a multiplicity of logical local ports supporting disparate communication protocols. The hub determines 406 whether or not the detected entity is a PPC. If not a PPC, the hub prevents 408 the entity from establishing a network connection, thereby preventing access to the LCN and central authority by the unauthorized entity.

If the detected entity is a PPC, the hub establishes 410 a network connection to the central authority via the logical network port of the hub. The hub facilitates 412 authentication of the PPC for use on the LCN, and access 414 to the central authority by the PPC. Authorized operations may then be performed 416 as between the PPC and central authority, such as interrogations, data transfers, and software updates.

Figure 7:
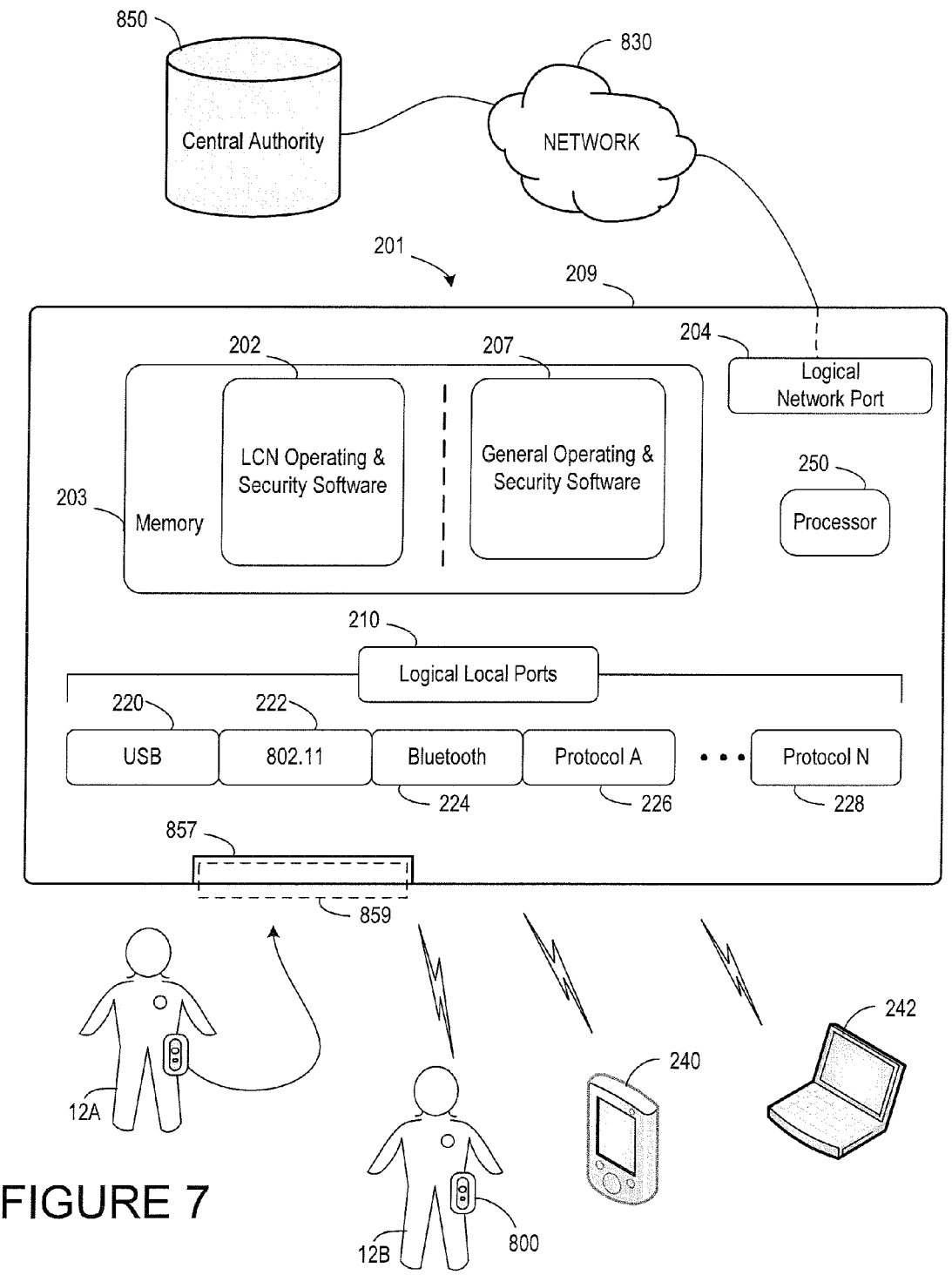
FIG. 7 is an illustration of a communications hub configured to effect connection for a number of PPCs and general internet access entities having different communication protocols to LCN and general internet target resources, respectively, in accordance with embodiments of the present invention.

FIG. 7 is an illustration of a communications hub that effects communication between a number of PPCs having different communication protocols and a central authority via an LCN in accordance with other embodiments of the present invention. The embodiment shown in FIG. 7 is similar to that shown in FIG. 5, and further provides a capability to facilitate access to the Internet or other non-LCN networks or resources. In this embodiment, the hub 201 allows non-LCN authorized entities to access the Internet in the same manner as conventional network hubs, switches, and routers. The hub 201 also facilitates LCN/CA access to PPCs and other authorized entities.

A hub 201 implemented in accordance with FIG. 7 finds particular utility in public locations where access to the Internet and an LCN is desired. Such public locations include malls, restaurants, coffee shops, governmental offices and buildings, schools, and the like.

The memory 203 of the hub 201 shown in FIG. 7 includes LCN software 202, as previously described, and general operating and security software 207. The LCN software 202 facilitate connectivity to an LCN and central authority for PPCs. The general software 207 facilitates Internet connectivity for generic entities, such as PDAs 240 and laptops 242. For example, the general software 207, when executed by processor 250, provides a connection mapping and authentication/authorization for generic Internet entities to target resources on the Internet or other network. There are several ways to facilitate non-LCN authorized entities access to target resources over the Internet, which depends on the particular manner of LCN connectivity. According to one approach in which a VPN is used to provide a connection to the LCN, non-LCN entity traffic can be routed over an Internet path instead of the VPN path.

Figure 8:
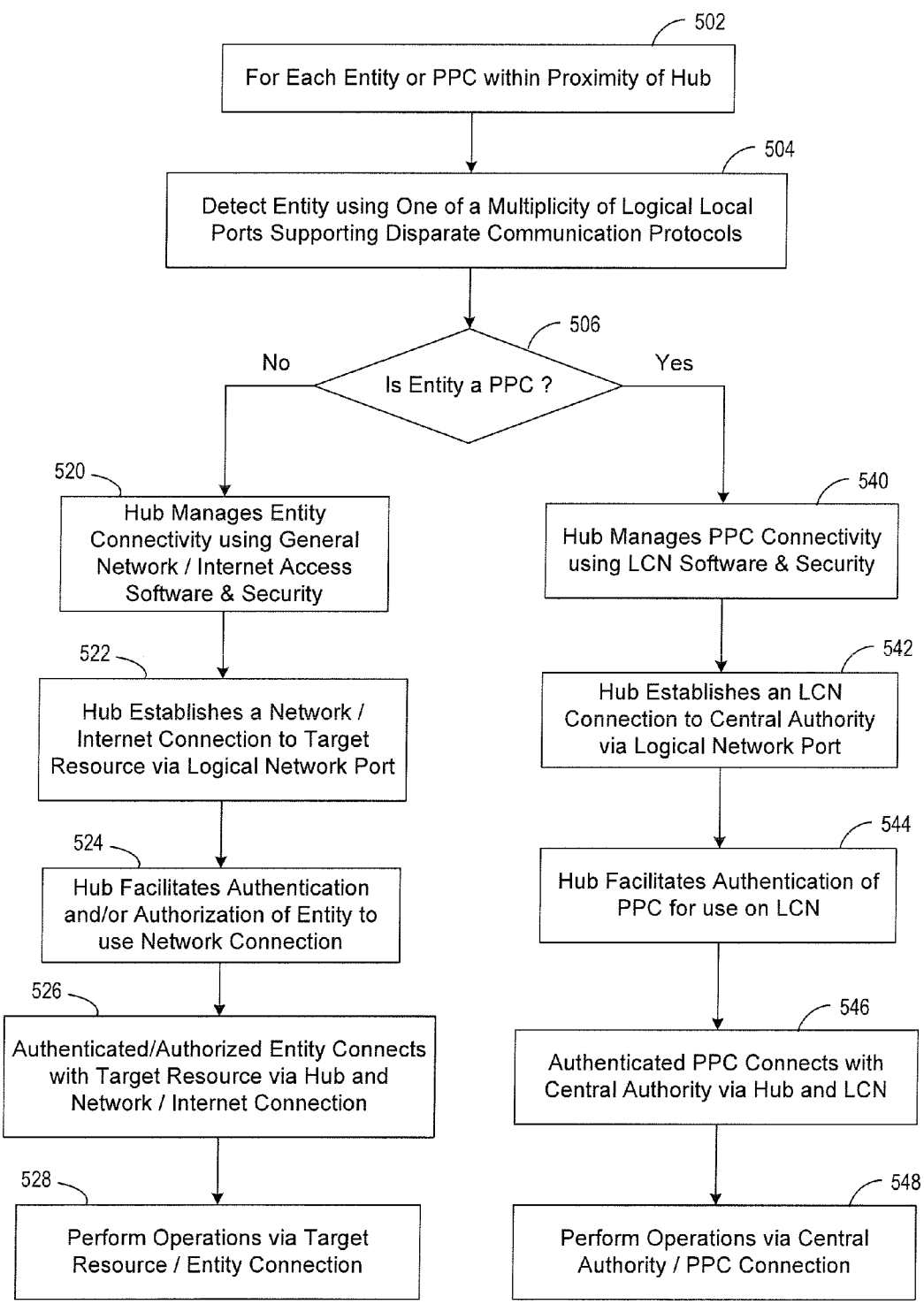
FIG. 8 is a flow chart of various processes for effecting communications between a number of PPCs and different general purpose entities and a CA and general internet target resources, respectively, via a communications hub and an LCN in accordance with embodiments of the present invention.

FIG. 8 is a flow chart showing various processes implemented by a hub having capabilities of that shown in FIG. 7 in accordance with embodiments of the present invention. For each entity or PPC that comes 502 into proximity with the hub, the hub detects 504 presence of the entity or PPC using one of a multiplicity of logical local ports supporting disparate communication protocols. The hub determines 506 whether or not the detected entity is a PPC. If the detected entity is a PPC, the hub manages 540 PPC connectivity using the LCN software executed by the hub's processor.

In this case, the hub establishes 542 a network connection to the central authority via the logical network port of the hub using the LCN software executed by the hub's processor. The hub facilitates authentication 544 of the PPC, access 546 to the central authority by the PPC, and performance 548 of various operations as between the central authority and the authenticated PPC.

If the hub determines that the detected entity is not a PPC or other LCN authorized entity, the hub manages 520 connectivity of the non-LCN authorized entity using the general network/Internet access and security software executed by the hub's processor. In this case, the hub establishes 522 a network/Internet connection to a target resource via the logical network port of the hub using the general software executed by the hub's processor. The hub facilitates authentication and/or authorization 524 of the entity, connection and/or access 526 to the target resource by the entity, and performance 528 of various operations as between the target resource and the entity.

Figure 9:
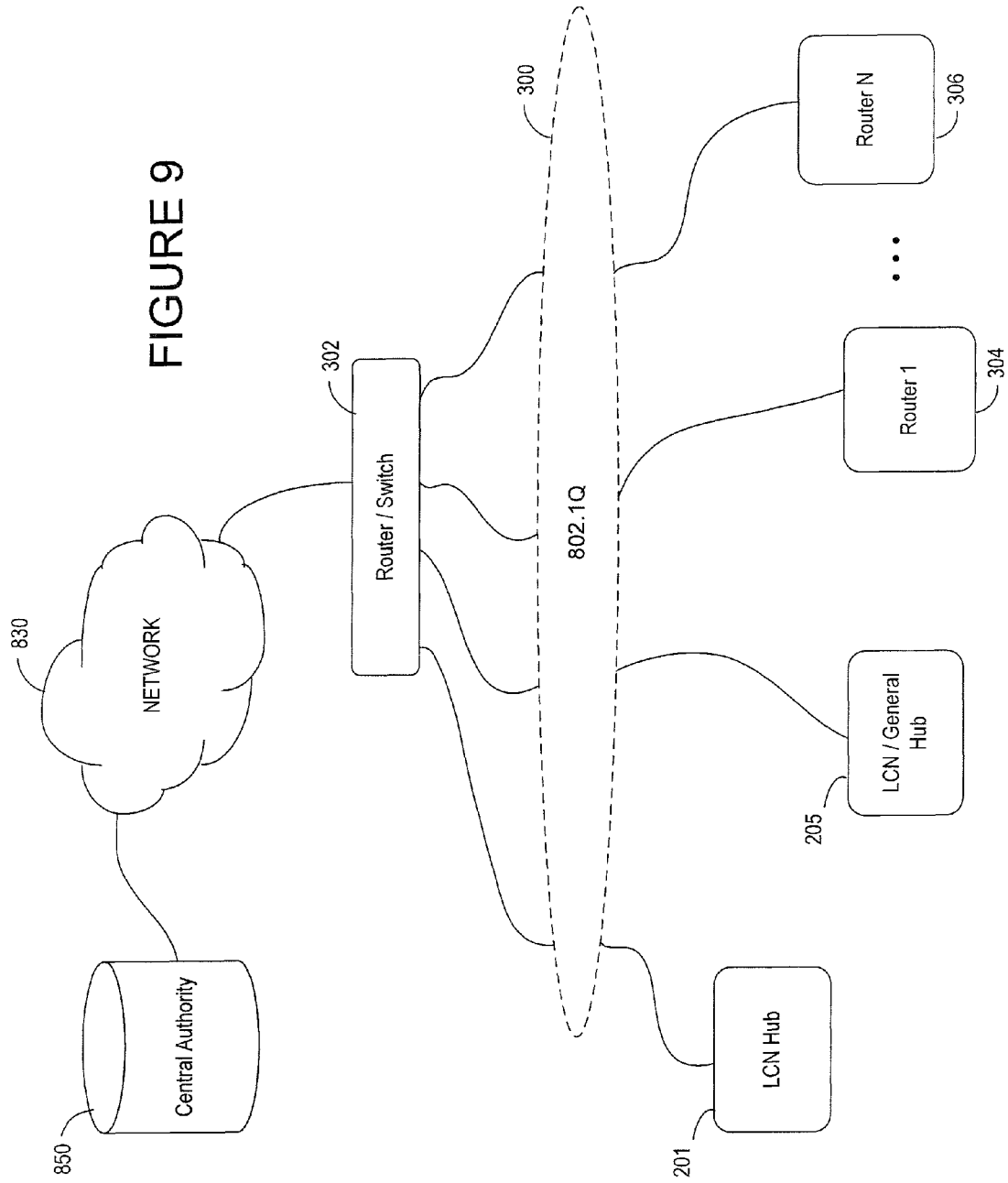
FIG. 9 is an illustration of a router/switch configured to effect connectivity between a number of PPCs and general internet access entities having different communication protocols to LCN and general internet target resources, respectively, in accordance with embodiments of the present invention.

FIG. 9 is an illustration of a conventional router, switch or hub that can be modified or upgraded to implement LCN operating and security software to provide secured access to an LCN/central authority in accordance with embodiments of the present invention. In some embodiments, a conventional router, switch or hub can be modified or upgraded to implement both LCN software to provide secured access to an LCN/central authority and general operating and security software to provide Internet or other network access. In accordance with FIG. 9, the router/switch 302 is intended to represent any conventional router, switch or hub that can be modified to implement LCN software.

Embodiments according to FIG. 9 advantageously allow medical device manufactures to use non-proprietary publically available communication devices (e.g., off-the-shelf or general purpose communication devices) for controlling access to an LCN/central authority and, if desire, to the Internet by PPCs and other entities. In this manner, a general purpose hub, switch or router, for example is transformed from a general purpose communications device (one that initially does not have or cannot execute LCN software) to function as a special purpose communications device (one that has and can execute LCN software). Embodiments according to FIG. 9 can significantly reduce the cost and complexity of LCN implementations.

The router/switch 302 shown in FIG. 9 preferably implements a communications mechanism that allows different hubs, switches, routers, and networks to connect with different network resources, including Internet, LCN, and other public and private/secured resources, while maintaining security requirements of each connection. According to some embodiments, the router/switch 302 is configured to implement an IEEE 802.1Q protocol, also referred to as virtual LAN (VLAN) tagging. VLAN tagging provides a mechanism to allow multiple bridged networks to transparently share the same physical network link without leakage of information between networks.

In the representative embodiment shown in FIG. 9, the router/switch 302 facilitates communication between network 830 and an LCN hub 200, an LCN/general access hub 201, and router 304, 306 of the same or different configuration. The VLAN protocol of the router/switch 302 ensures that each entity 200, 201, 304, 306 has access only to those network resources, including the central authority 850, that are authorized for each entity. In this way, integrity of an LCN can be maintained while providing access to a myriad of disparate entities to Internet and other public or private resources.

Figure 10:
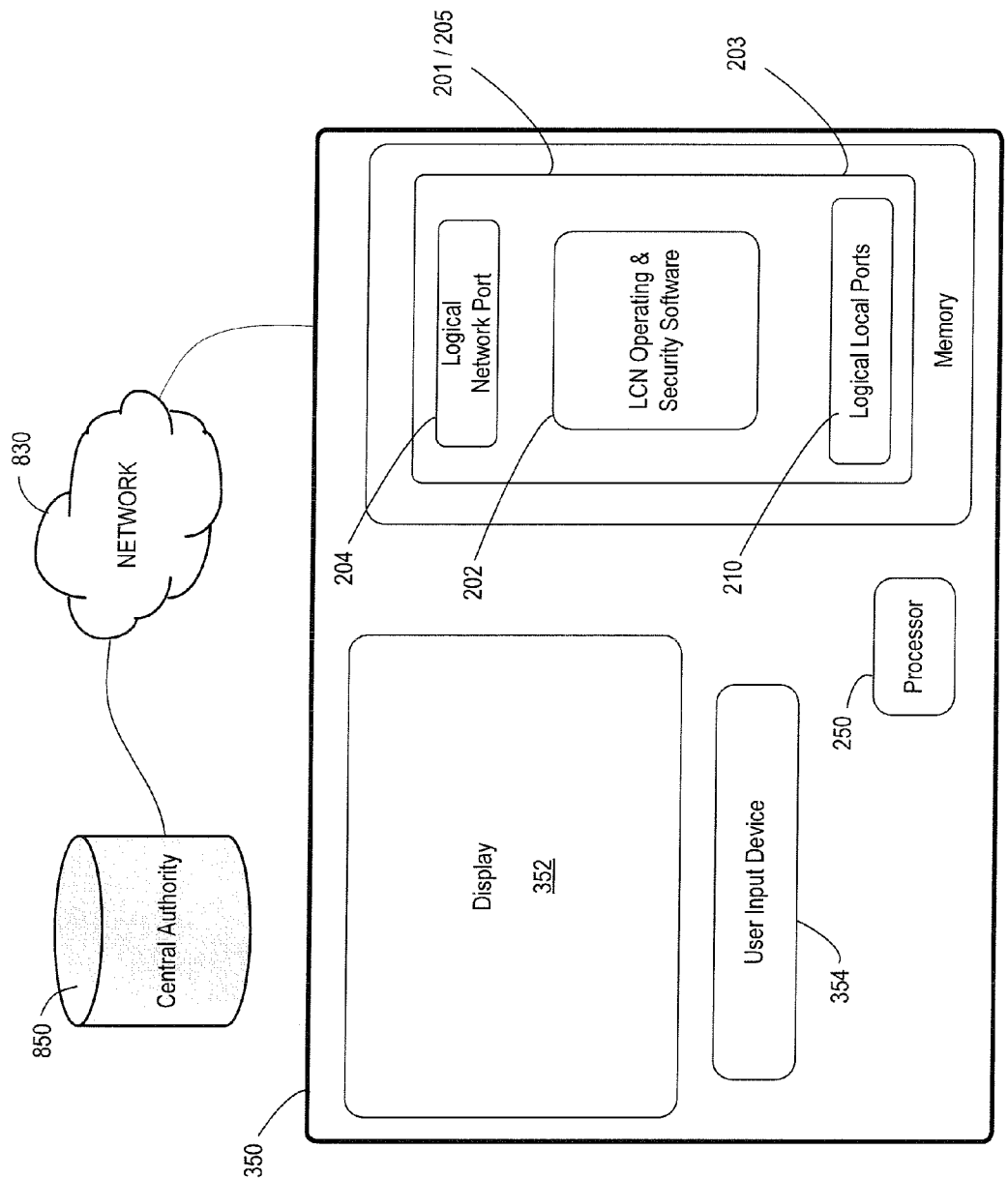
FIG. 10 is an illustration of a programmer configured to communicate with a number of PPCs having different communication protocols and to transmit medical data to and from a CA in a secured manner via an LCN in accordance with embodiments of the present invention.

Turning now to FIG. 10, there is shown an embodiment of an implantable medical device programmer that incorporates components and features of an LCN hub as previously described in accordance with embodiments of the present invention. The programmer 350 shown in FIG. 10 is generally configured to include components and features equivalent or similar to those of conventional programmers, such as those used to program cardiac rhythm management devices (e.g., pacemakers, ICDs, CRT devices). Such components and features include a display 352, a user input device 354 (e.g., keyboard, stylus, mouse, etc.), a wireless or wand-based communications facility, printer, and an input/output interface, among other components and features.

The programmer 350 shown in FIG. 10 further includes a logical network port 204 adapted to effect communications between the programmer 350 and the CA 850 via the unsecured network 830. A multiplicity of logical local ports 210 are provided to implement various disparate communication protocols for effecting connectivity between the programmer 350 and a multiplicity of PPCs 800. Memory 203 of the programmer 350 is configured to store life critical network software 202 comprising program instructions which, when executed by the processor 250, cause the processor 250 to determine that entities requesting a network connection via the programmer 350 are PPCs 800. The processor 250 of the programmer 350, when executing LCN software 202, authenticates requesting PPCs 800 to the CA 850, and enables communication between the PPCs 800 and CA 850 via the logical local ports 210 and a logical network port 204 upon successful authentication.

Figure 11:
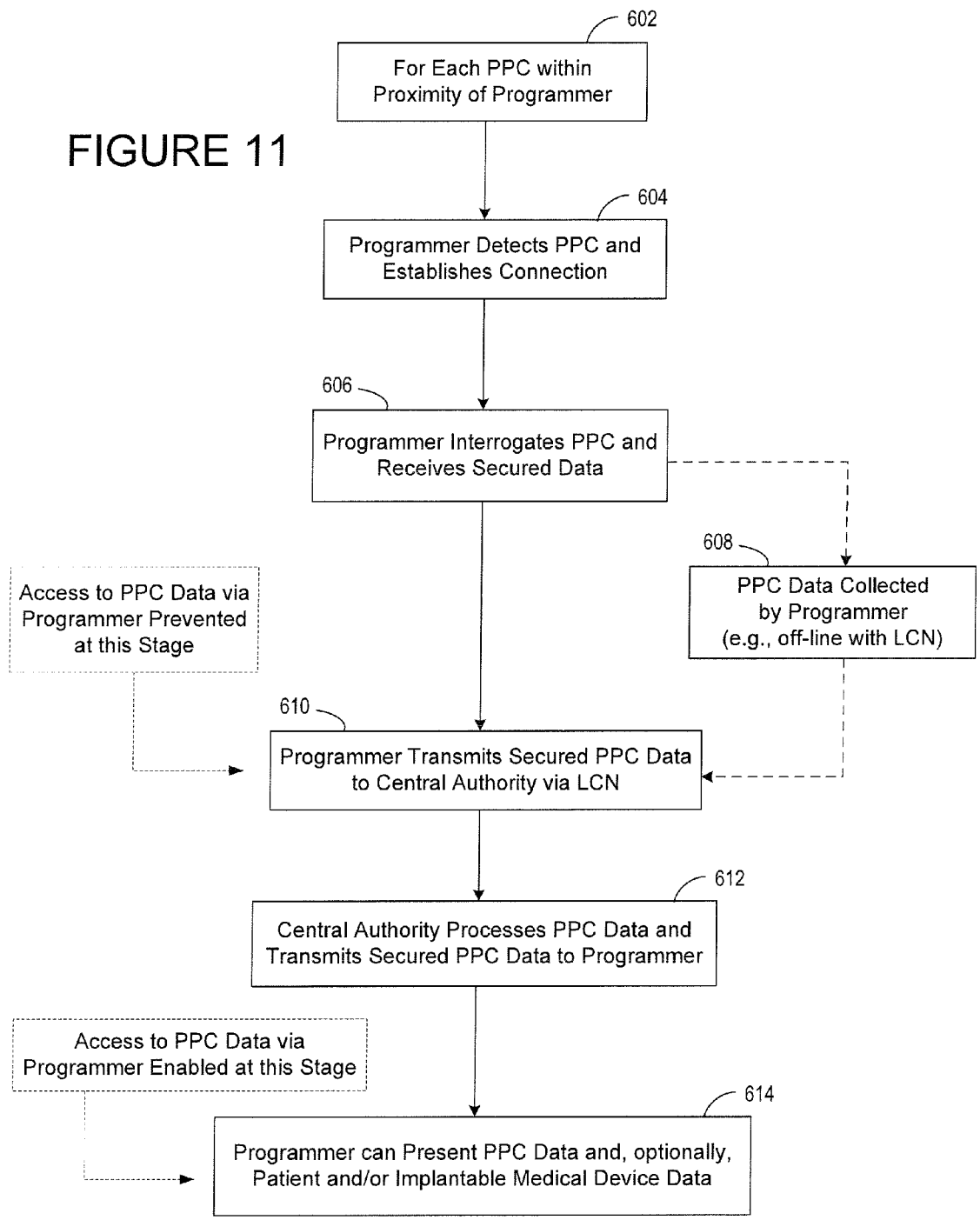
FIG. 11 is a flow chart of various processes for effecting communications between a number of PPCs having different communication protocols and a CA via a programmer and an LCN in accordance with embodiments of the present invention.

FIG. 11 is a flow chart of various processes that may be implemented by an LCN programmer of the type shown in FIG. 10 in accordance with embodiments of the present invention. In FIG. 11, it is assumed that the programmer permits only PPCs and other LCN authorized entities to gain access to an LCN/central authority. It is also assumed that the programmer is itself connected and authenticated to the LCN/central authority.

For each PPC (or LCN authorized entity) that comes 602 into proximity with the programmer, the programmer detects 604 presence of the PPC using one of a multiplicity of logical local ports supporting disparate communication protocols. The programmer interrogates 606 the PPC and receives data from the PPC. Preferably, the programmer transmits a request to the PPC that the PPC perform an interrogation of the PIMD. The PPC's processor executes medical firmware program instructions to securely interrogate the PIMD and acquire PIMD data from a patient's implantable medical device, preferably in compliance with the Health Insurance Portability and Accountability Act (HIPPA) and other laws and regulations that can require special procedures for handling of medical data (e.g., requirements of an FDA Class III medical device).

The PPC data typically includes data acquired from a patient's implantable medical device and, in some embodiments, other implantable or external sensors/devices by the PPC. This data is preferably encrypted or otherwise secured by the PPC (or the PIMD) so that the programmer is initially unable to decipher most or all of the data received from the PPC. The interrogation of the PPC/PIMD generally occurs in real-time with the programmer communicatively coupled to the LCN/CA. The interrogation may also be conducted and PPC/PIMD data collected 608 by the programmer in cases where the programmer is not connected to the LCN/CA or such connection is intermittent or of poor quality.

When connected to the LCN/CA, the programmer transmits 610 the secured PPC data to the CA via the LCN. The CA decrypts and processes 612 the received PCC data. The CA encrypts or otherwise secures the processed PPC data and then transmits 612 this data back to the programmer. The programmer may then access 614 the CA-processed PPC data, such as for presentation on the programmer's display and/or printing via the programmer's printer. The CA-processed PPC data received from the CA by the programmer may include patient and/or PIMD data that may be accessed by the programmer. Various operations impacting the programmer, PPC, and/or the PIMD may be implemented via communications between the CA and the PPC, such as software updates.

Figure 12:
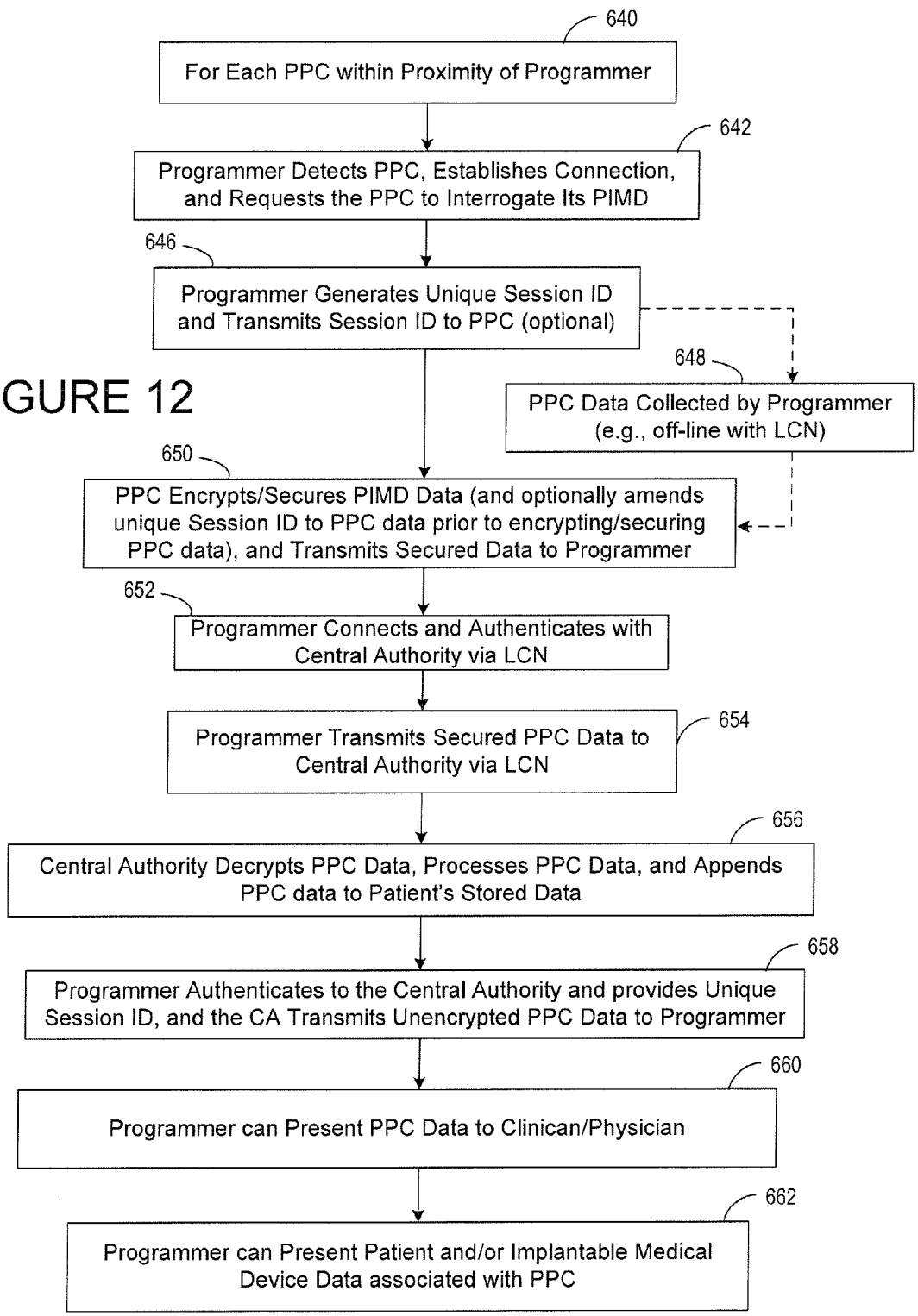
FIG. 12 is a flow chart of various processes for effecting communications between a number of PPCs having different communication protocols and a CA via a programmer and an LCN in accordance with various embodiments of the present invention.

FIG. 12 is a flow chart of various processes that may be implemented by an LCN programmer of the type shown in FIG. 10 in accordance with other embodiments of the present invention. As in the embodiment shown in FIG. 11, it is assumed that the programmer permits only PPCs and other LCN authorized entities to gain access to an LCN/central authority. It is also assumed that the programmer is itself connected and authenticated to the LCN/central authority.

For each PPC (or LCN authorized entity) that comes 640 into proximity with the programmer, the programmer detects 642 presence of the PPC using one of a multiplicity of logical local ports supporting disparate communication protocols. The programmer initiates PPC/PIMD interrogation, which preferably involves the programmer transmitting a signal to the PPC requesting the PCC to interrogate its PIMD. Data acquired and/or produced by the PPC is preferably encrypted or otherwise secured 650 by the PPC so that the programmer is initially unable to decipher most or all of this data. According to one approach, the PPC encrypts the PPC data using the CA's public key. This ensures that only the CA can decrypt the PPC data. Interrogation of the PPC/PIMD generally occurs in real-time with the programmer communicatively coupled to the LCN/CA. The interrogation may also be conducted and PPC/PIMD data collected 648 by the programmer in cases where the programmer is not connected to the LCN/CA or such connection is intermittent or of poor quality.

In cases where the programmer has a legitimate need for the PPC data (e.g., when PIMD data is needed by an ER physician), the programmer generates 646 a unique session ID code and transmits the session ID code to the PPC. The session ID code is amended 650 to the PPC data prior to encryption. Generation and use of a session ID code is considered optional, since it is contemplated that, in many instances, the programmer will be used to communicate PPC data to the CA without need for local displaying or printing of the PPC data.

The programmer, if not already connected, establishes 652 connectivity with, and authenticates to, the CA via an LCN connection. The programmer transmits 654 the secured PPC data to the CA via the LCN. In cases where a session ID code is generated, this code is incorporated in the secured PPC data that is transmitted from the programmer to the CA. In some embodiments, the PPC, rather than the programmer, connects and authenticates with the CA via the LCN, and transmits the PPC data (and any programmer data) to the CA. In some configurations, the programmer and the PPC are capable of facilitating transmission of PPC data between the PPC and the CA, thereby providing redundancy in PPC-to-CA connectivity options. In other configurations, only the PPC (and not the programmer) is capable of facilitating transmission of PPC data between the PPC and the CA, which may be the case in reduced cost programmer implementations.

The CA decrypts 656 the secured PPC data, preferably by use of the CA's private key, and performs processes 656 to ensure that the PPC data is associated with an authorized PPC and that the received PPC data includes a session ID code, if any. The CA associates the received PPC data with a patient record, and appends the received PPC data to the patient's data record file.

In cases where the programmer has a legitimate need for PPC data, the programmer (directly or indirectly via the PPC), if not already connected, establishes 658 a connection with, and authenticates to, the CA. The programmer provides the session ID code to the CA. The CA returns the PPC data (and possibly patient or other data) to the programmer in an unencrypted format. The unencrypted PPC data received from the CA may be accessed 660 at the programmer, such as for presentation on the programmer's display or printer for review by a clinician or physician. If other data is included with the unencrypted PPC data, such as trended PIMD data and other patient information, the data may also be accessed 662 at the programmer, such as for displaying or printing. Various operations impacting the programmer, PPC, and/or the PIMD may be implemented via communications between the CA and the programmer/PPC, such as software updates.

Embodiments of the invention implemented in accordance with FIGS. 10-12 provide a number of advantage and benefits. When a patient walks into the clinic, for example, the staff is immediately informed of the patient's arrival and are presented with up-to-date information about the patient. This information can be reviewed by the clinic's staff before the patient is brought to the examine room. This improved clinic work-flow. In emergency rooms, ER physicians do not need to understand the detailed operation of the programmer. Most ER physicians are untrained in the use of implantable medical device programmers, and will call an electrophysiologist or cardiologist when a patient arrives having an IPG with possible heart related issues.

Figure 13:
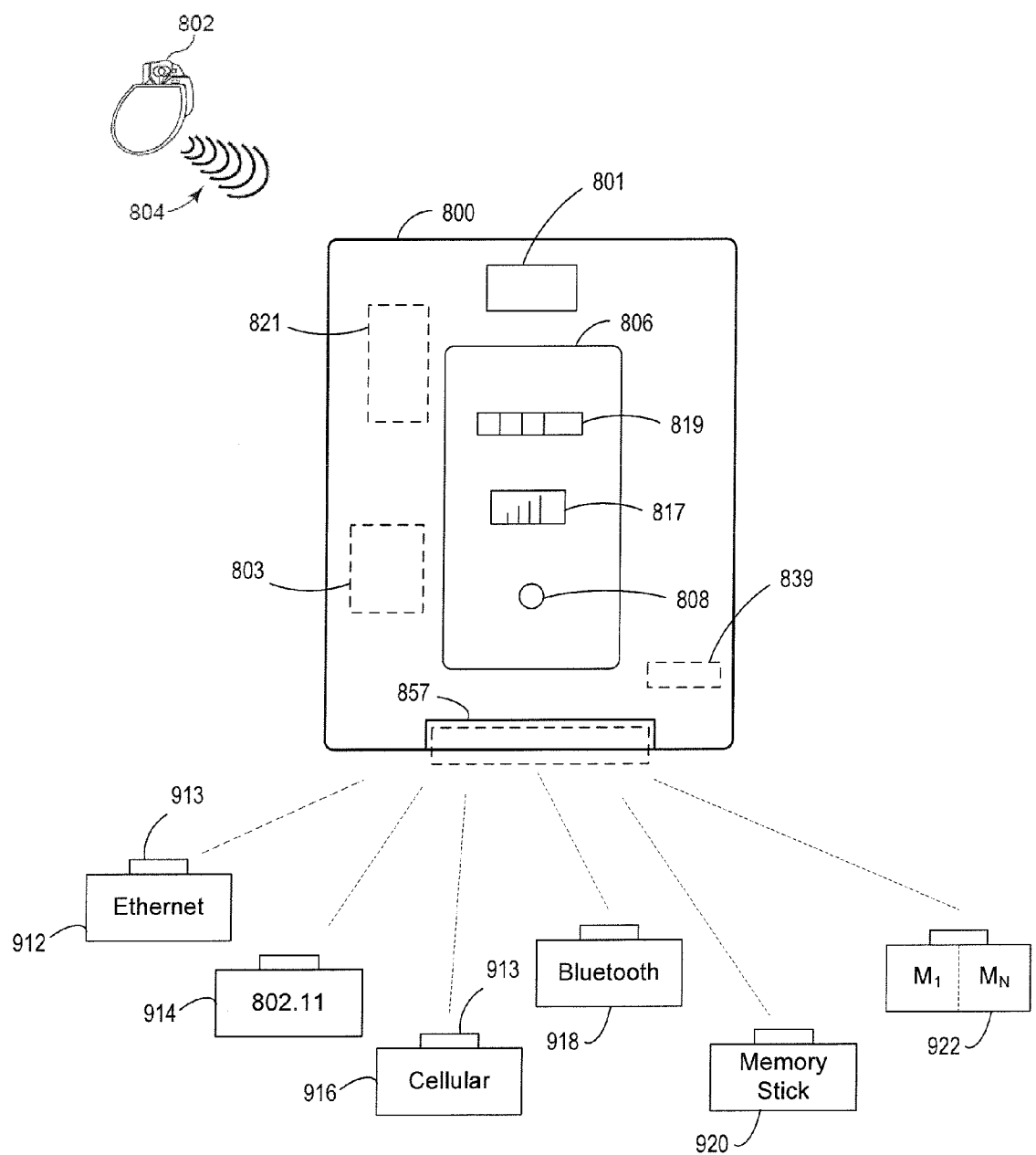
FIG. 13 is an illustration of a modular PPC implemented to receive one or more modules each configured to effect communications using different communication protocols and/or provide enhanced PPC capabilities in accordance with embodiments of the present invention.

FIG. 13 is an illustration of a modular PPC implemented to receive one or more modules each configured to effect communications using different communication protocols and/or provide enhanced PPC capabilities in accordance with embodiments of the present invention. As discussed previously, a modular PPC typically includes sufficient hardware and software to be able to interrogate a PIMD, and effects communications with an external device, system or network only by way of a universal communications port. As such, modular PPC embodiments of the present invention preferably exclude a built-in communications facility to communicate with external devices, systems, and networks. In this regard, communications between the modular PPC and an external device, system or network can be effected only by physically connecting a communications-enabled module or communications cable/connector to the universal communications port of the PPC.

The PPC 800 shown in FIG. 13 includes a simple display 806, which includes a battery status indicator 819, a signal strength indicator 817, and a push button 801. The PPC 800 may include an alert module 839 that generates an alert signal in response to a condition requiring immediate attention. The alert module 839 may be coupled to a visual, audible or vibratory component of the PPC 800. The PPC 800 includes a processor 250 coupled to memory 203. Memory 203 is preferably configured to store various firmware, software, and data, including software for accessing the LCN/CA and firmware for interrogating a PIMD (e.g., medical software or firmware).

FIG. 13 further shows a multiplicity of modules 912-922 each equipped with a universal port connector 913 configured to be received by the universal communications port 857 of the PPC 800 (as is partially depicted by a module's universal port connector, shown as a dashed block, being received by the PPC's universal port 857). Each of the modules 912-992 shown in FIG. 13 provides a different communications capability or other functional enhancement. These modules include an Ethernet module 912, an 802.11 module 914, a cellular module 916, a Bluetooth module 918, and a memory stick 920. Module 922 illustrates provision of multiple sub-modules $M_1$ and $M_2$ incorporated into a single module package. Modules of various types may be stacked or otherwise combined to form a single multi-function module 922.

Figure 14:
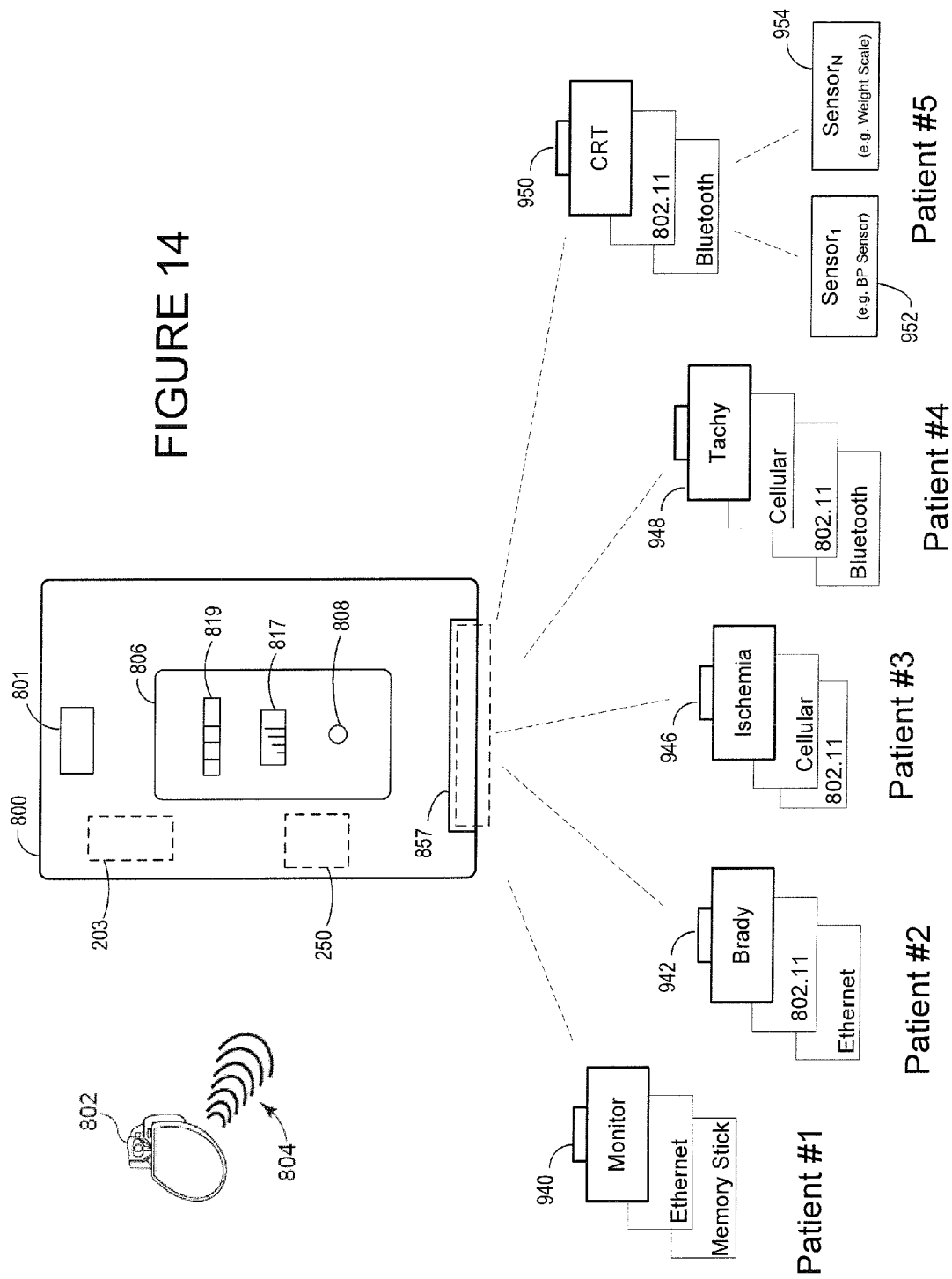
FIG. 14 is an illustration of a modular PPC tailorable for specific patients having particular medical conditions and configured to receive one or more modules each configured to effect communications using different communication protocols and/or provide enhanced PPC capabilities in accordance with embodiments of the present invention.

FIG. 14 is an illustration of a modular PPC tailorable for specific patients having particular medical conditions and configured to receive one or more detachable modules of the type described with reference to FIG. 13 and other figures in accordance with embodiments of the present invention. FIG.

14 shows different combinations of modules that are tailored for five patients having different medical conditions.

The module 940, for example, is tailored for conducting cardiac monitoring for Patient #1. In this representative illustration, Patient #1 has a fairly benign form of cardiac arrhythmia (e.g., PVCs, PACs), which requires minimal monitoring by the patient's physician (via the LCN/CA). As such, module 940 includes an Ethernet communications facility and a memory stick. The memory stick provides extra memory for storing PIMD data acquired by the PPC 800, and the Ethernet communications facility allows for LCN/CA connectivity, which may be relatively infrequent for Patient #1.

The module 942 is tailored for Patient #2, who has a bradycardia condition. Patient #2 may require more frequent monitoring by the physician. As such, module 942 is equipped with two different communications facilitates which, in this example, include a wireless facility (802.11) and a wired communications facility (Ethernet). Patient #3, by way of further example, has a more serious Ischemia condition, which requires an increased number of connectivity options for connecting with the LCN/CA. In this representative example, the module 946 for Patient #3 includes a cellular and short-range wireless (802.11) communications facility. Patient #4 has a relatively serious ventricular tachycardia condition, which requires an increased number of connectivity options for connecting with the LCN/CA. As such, the module 948 for Patient #4 includes three different communications facilities, including cellular, short-range wireless (802.11), and Bluetooth communications facilities.

Patient #5 has a progressive heart failure condition which is treated using a CRT device. Module 950 is tailored to provide enhanced features for this patient. In this illustrative example, Patient #5 is relatively immobile, living in a nursing facility that provides WiFi Internet access. The module 950 for Patient #5 need only include a single short-range wireless communications capability (802.11). However, Patient #5 requires frequent monitoring of blood pressure, heart rate, and other sensor information (e.g., weight scale data, respiration data, blood gas saturation data, etc.). The module 950 includes a Bluetooth communications facility to effect connectivity between the PPC 800 and various sensors, such as sensors 952 and 954. Data acquired by the PPC 800 for each of the patient scenarios shown in FIG. 14 is communicated to the LCN/PA based on criticality, connection quality, and connection cost, among other factors.

Figure 15:
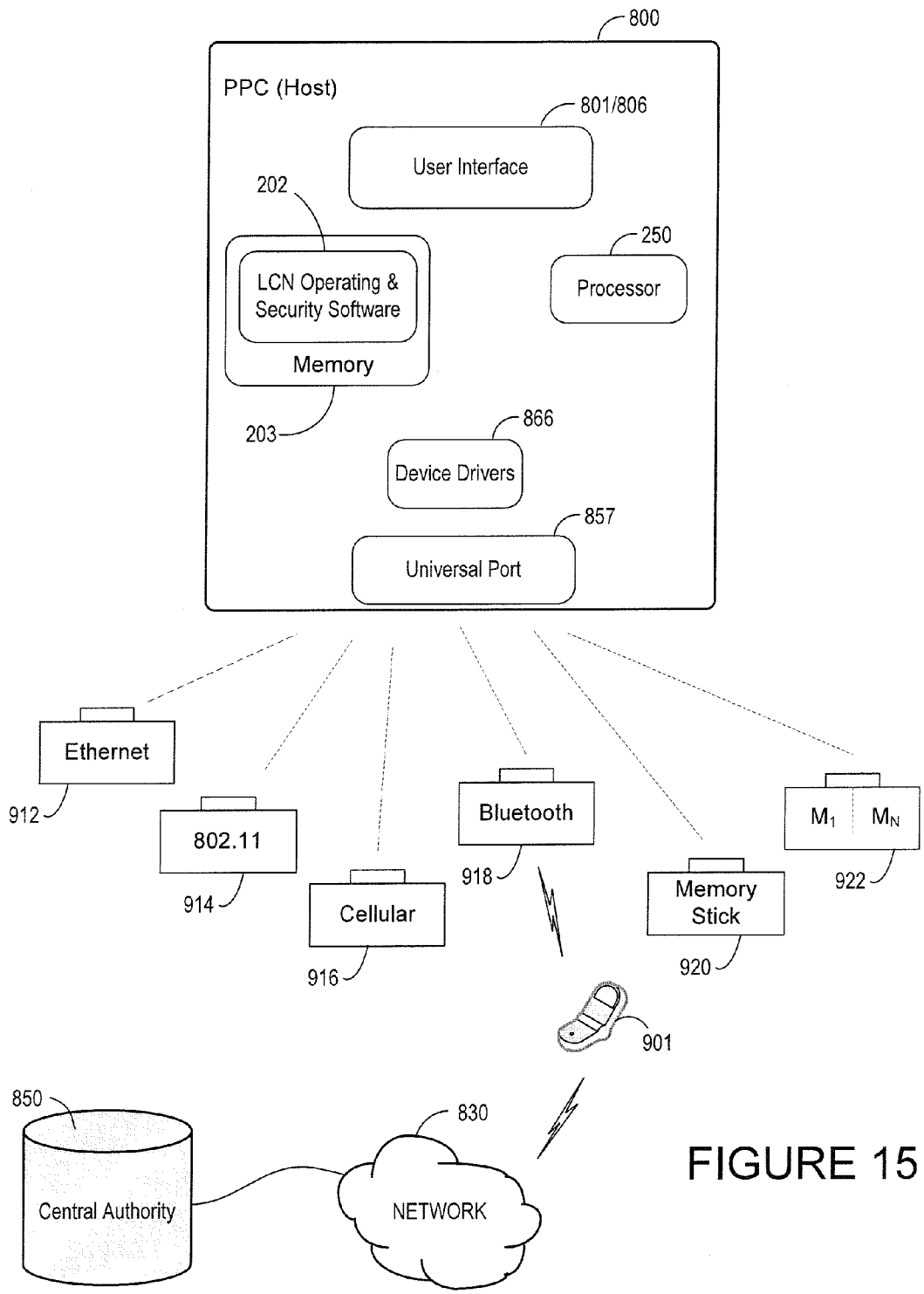
FIG. 15 is an illustration of a modular PPC configured as a USB host and to receive one or more modules each configured to effect communications using different communication protocols and/or provide enhanced PPC capabilities in accordance with embodiments of the present invention.

FIG. 15 is an illustration of a modular PPC configurable as a USB host to receive one or more modules each configured to effect communications using different communication protocols and/or provide enhanced PPC capabilities in accordance with embodiments of the present invention. The PPC 800 illustrated in FIG. 15 is equivalent or similar to PPCs described previously with reference to other figures of the disclosure. FIG. 15 shows device drivers 866 that are available or uploaded to the PPC's memory 203 to facilitate connectivity with various modules via the universal communications port 850. Also shown in FIG. 15 is an extended communications capability provided by a Bluetooth module 918 which communicatively couples to a cell phone 901 to access the network 830 and CA 850.

Figure 16:
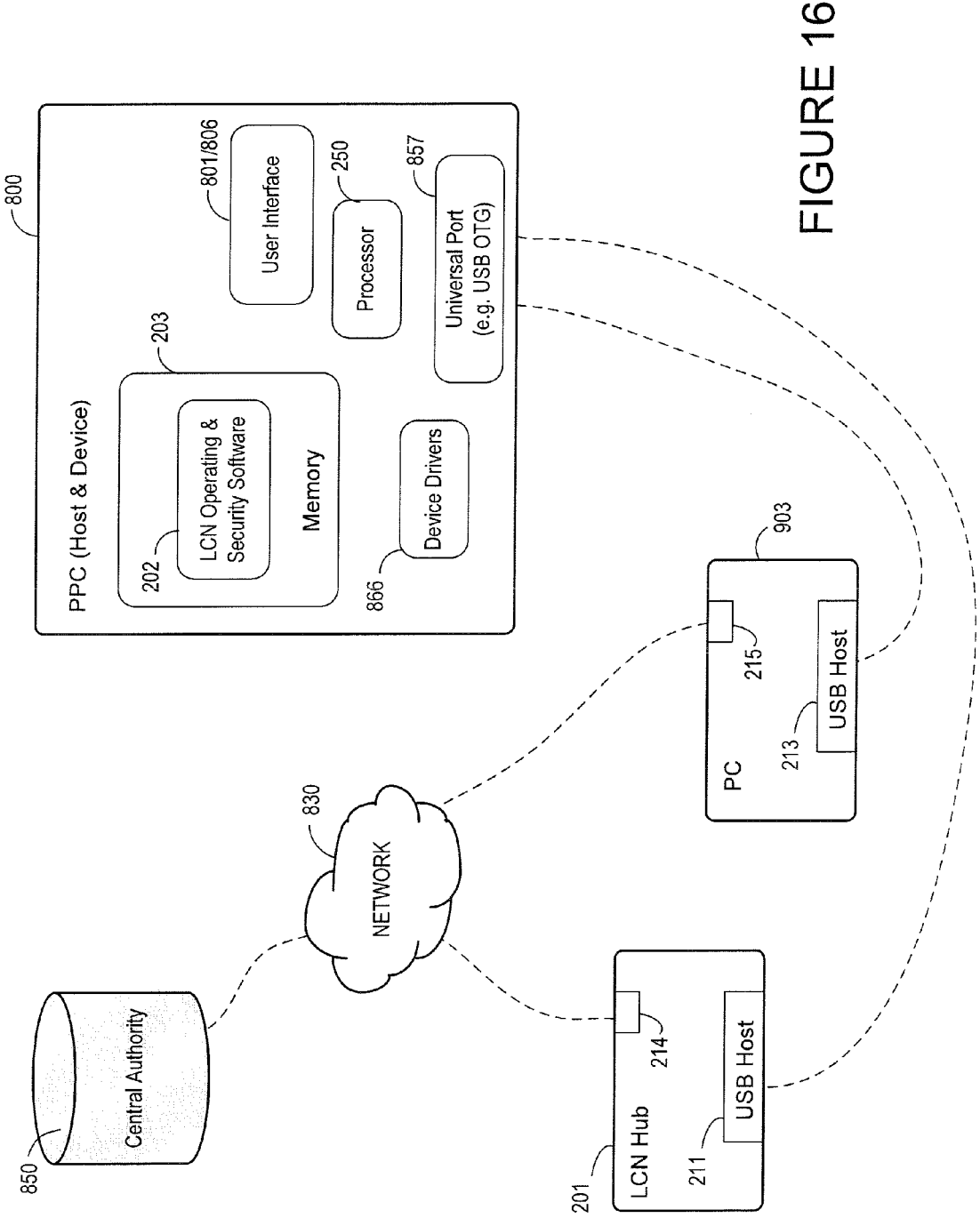
FIG. 16 is an illustration of a modular PPC configured as a USB host and a USB device, and to receive one or more modules each configured to effect communications using different communication protocols and/or provide enhanced PPC capabilities in accordance with embodiments of the present invention.

FIG. 16 is an illustration of a modular PPC configured as a USB host and a USB device, and to receive one or more modules each configured to effect communications using different communication protocols and/or provide to enhanced PPC capabilities in accordance with embodiments of the present invention. The PPC 800 illustrated in FIG. 16 is equivalent or similar to PPC host implementations described previously with reference to other figures of the disclosure.

In the illustrative embodiment shown in FIG. 16, the PPC 800 operates as a USB host in the manner shown in FIG. 15, for example. The PPC 800 of FIG. 16 also operates as a USB device, such as by implementing a USB-OTG protocol via universal communications port 857.

FIG. 16 shows two possible connection scenarios involving two different USB hosts. One connection scenario involves a USB host 213 of a PC 903. The other connection scenario involves a USB host 211 of an LCN hub 201. Wireless or wired connections may be established between the PPC's universal communications port 857 and USB host interfaces 211, 213 of PC 903 and LCN hub 201/205, respectively. The PC 903 and LCN hub 201/205 are preferably configure to provide access to network 830/CA 850 via a logical network port 215, 214.

Figure 17:
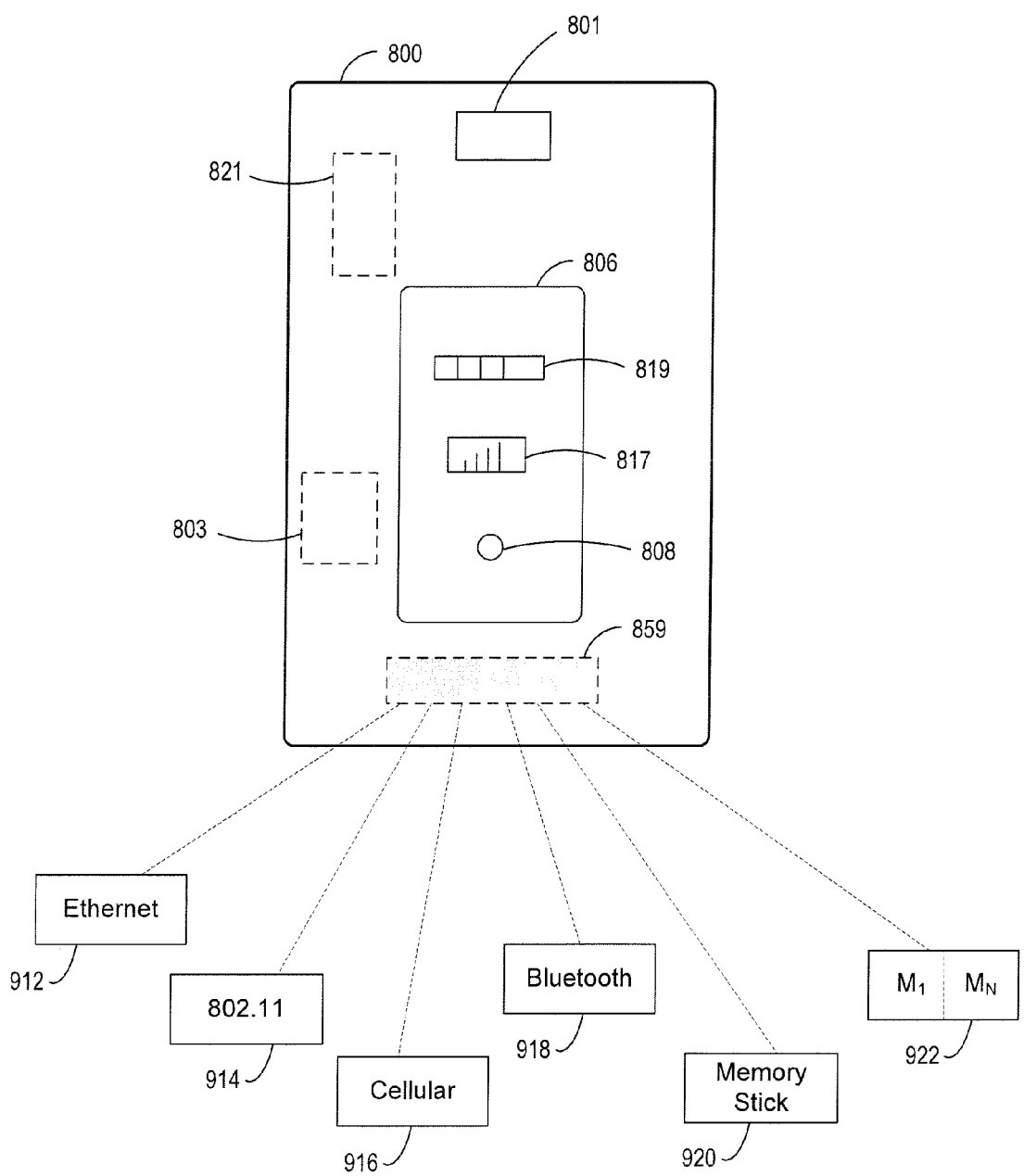
FIG. 17 is an illustration of a modular PPC having module functionality implemented in PPC circuitry to effect communications using different communication protocols and/or provide enhanced PPC capabilities in accordance with embodiments of the present invention.

FIG. 17 is an illustration of a modular PPC having configurable modules implemented in PPC circuitry to effect communications using different communication protocols and/or provide enhanced PPC capabilities in accordance with embodiments of the present invention. Instead of being incorporated in a detachable add-on module, circuitry of one or more of modules 912-922 may be incorporated in the PPC's internal circuitry 859 (i.e., the PPC's PCB). In other embodiments, one or more of modules 912-922 may be incorporated in the PPC's internal circuitry 859, and one or more detachable modules may be coupled to the PPC 800 by way of a universal communications port (not shown) provided on the PPC 800. In this case, a standard set of communications capabilities can be built into the PPC 800, while other capabilities can be provided via attachment of add-on modules to the PPC's universal communications port.

Figure 18:
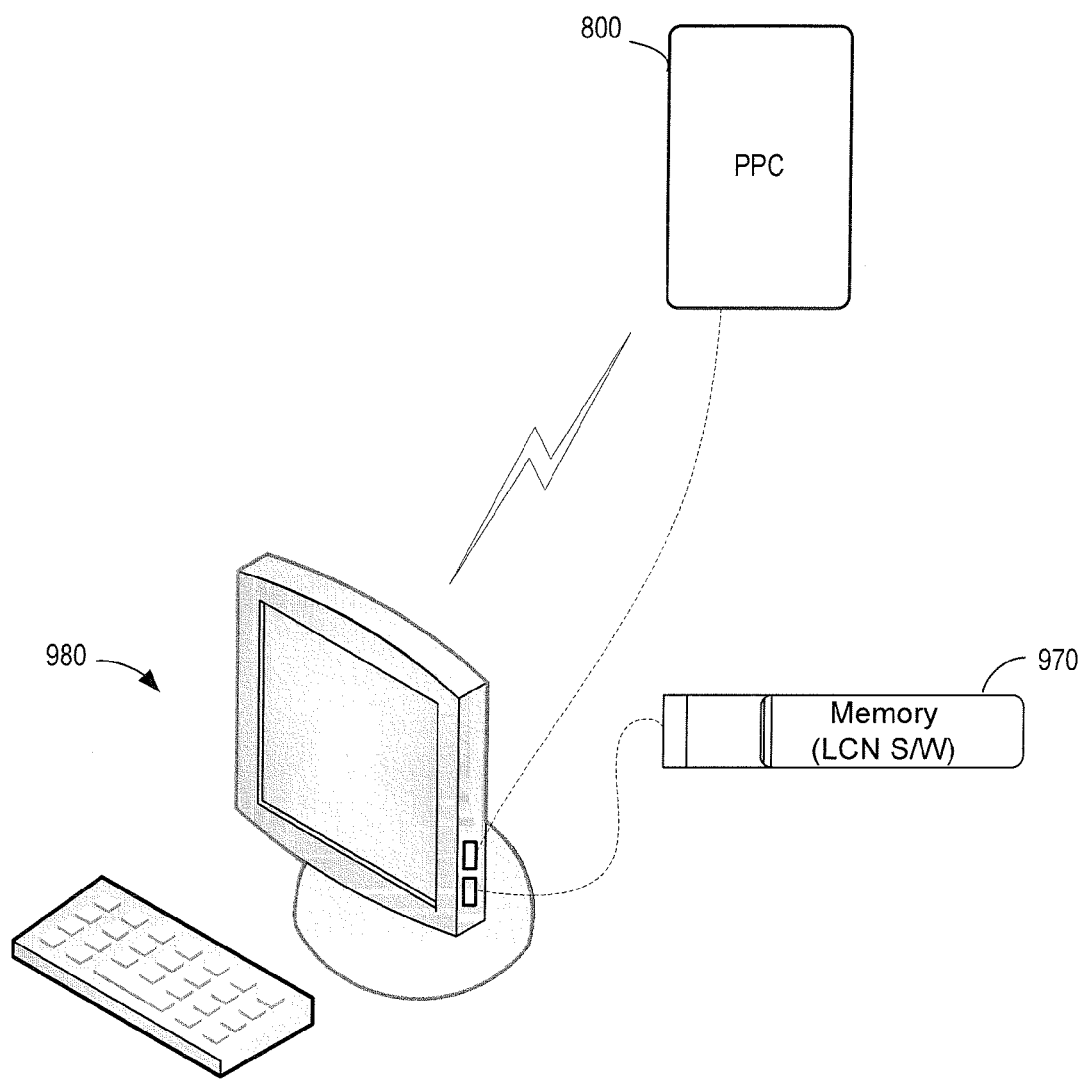
FIG. 18 illustrates an embodiment of a PPC configured with software that recognizes a special dongle, the dongle configured to detachably connect to a computer via a universal interface in accordance with embodiments of the present invention.

FIG. 18 illustrates an embodiment of a PPC 800 configured with software that recognizes a special dongle 970, such as a USB dongle. The dongle 970 is configured to detachably connect to a computer 980 via a universal communications interface (e.g., a USB port). This connection can be a wired or wireless connection. The dongle 970 preferably stores a unique code in a secure area of the dongle's non-volatile memory that uniquely identifies the dongle as a "PPC key device." The USB dongle 970 is preferably universal in configuration and protocol, and enables special modes and/or features of the PPC. The dongle software may be of various forms that allow a tier of special features on the PPC as security allows. According to some embodiments, a dongle 970 may be implemented as a USB programming dongle. PPC and/or LCN software stored in the dongle 970 may be transferred to the PC 980 based on proper authorization. Software transferred to the PC 980 from the dongle 970 may enable any number of programming capabilities for controlling the operations/functions of the PPC 800 and/or PIMD that is accessed via the PPC 800.

According to embodiments consistent with FIG. 18, a modular PPC system of the present invention includes a modular PPC of the type previously described and a dongle configured to communicate with the modular PPC. For example, the dongle may be configured to include a connector, circuitry, and memory. The connector of the dongle is configured to detachably engage and establish signal connectivity with a communications port (e.g., USB port) of a computer physically separate from the modular PPC. A detachable module stores program instructions for effecting communications with the circuitry of the dongle which, when connected to the computer's communications port, establishes a communications link between the computer and the modular PPC.

The memory of the dongle preferably stores a unique code that uniquely identifies the dongle as an authorized PPC device. The memory of the dongle also stores program instructions which, when executed by the computer, enable predetermined modes of the PPC, such as programming modes, interrogation modes, diagnostics modes, software/firmware update modes (e.g., for updates, upgrades, patches), and other modes affecting the functionality and/or operation of the PPC. The dongle software may enable "programmer-like" capabilities on the computer, such as PIMD data review, displaying, printing, or outputting to another device, system, or network. The dongle software may enable a computer (e.g., laptop, PDA, tablet PC) to operate as an LCN hub or an LCN programmer as described hereinabove.

According to various embodiments, including those described hereinabove, components of a life critical network may incorporate various methodologies for providing secure and reliable communication, including features described in one or more of the following references: U.S. Patent Publication Nos. 20070118188 and 20070083246, and U.S. Pat. Nos. 7,218,969; 7,203,545; 8,041,032; 8,027,727; 8,160,704; 7,801,620; 7,805,199; 7,218,969; and 7,751,901, all of which are incorporated herein by reference. Data originating at the PPC may be stored and/or analyzed at the central authority, which may include an APM server system, and which may be further coupled to one or more client stations to perform input and output functions. Methods, structures, and/or techniques described herein, may incorporate various APM server system related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference. Data acquired from a PIMD by a PPC and stored in an APM server may be transferred to, and incorporated within, an electronic medical records system, such as that disclosed in commonly owned U.S. Patent Publication No. 20070226013, which is incorporated herein by reference.

Using the description provided herein, embodiments of the invention may be implemented as a machine, process, or article of manufacture by using standard programming and/or engineering techniques to produce programming software, firmware, hardware or any combination thereof. Any resulting program(s), having computer-readable program code, may be embodied on one or more computer-usable media such as resident memory devices, smart cards or other removable memory devices, or transmitting devices, thereby making a computer program product or article of manufacture according to the invention. As such, the terms "article of manufacture," "computer program product," "computer-readable media" and other similar terms as used herein are intended to encompass a computer program that exists permanently or temporarily on any computer-usable medium or in any transmitting medium which transmits such a program.

As indicated above, memory/storage devices include, but are not limited to, disks, optical disks, removable memory devices such as smart cards, SIMs, WIMs, semiconductor memories such as RAM, ROM, PROMS, etc. Transmitting mediums include, but are not limited to, transmissions via wireless/radio wave communication networks, the Internet, intranets, telephone/modem-based network communication, hard-wired/cabled communication network, satellite communication, and other stationary or mobile network systems/communication links.

By way of example, and in accordance with various embodiments, a computer-readable medium of the present invention includes instructions stored thereon which are executable by a data processing arrangement disposed in a modular PPC. The program instructions stored on the medium causes the data processing arrangement to establish signal connectivity between a universal communications port of the PPC and at least one detachable module of a multiplicity of disparate detachable modules when mechanically connected to the universal communications port. At least some of the detachable modules are configured to provide the PPC with an external communications facility and have disparate communication protocols. The PPC is preferably devoid of a facility to effect external communications other than by way of a radio and the universal communications port of the PPC. The program instructions stored on the medium causes the data processing arrangement to execute life critical network (LCN) software stored on the medium to cause the PPC in cooperation with the at least one detachable module to transmit a request to a network access facility for a connection to an unsecured network, facilitate authentication of the PPC to a central authority (CA), and facilitate secured communication between the PPC and CA upon successful PPC authentication From the description provided herein, those skilled in the art are readily able to combine software created as described with appropriate general purpose or special purpose computer hardware to create a system and/or device and/or subcomponents embodying aspects of the invention, and to create a system and/or device and/or subcomponents for carrying out the methods of the invention.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A communications device for effecting secured communications between a plurality of portable patient communicators (PPC) and a central authority (CA), each of the plurality of PPCs configured to effect connectivity with a patient implantable medical device (PIMD), the communications device comprising:
  a housing;
  a logical network port provided at the housing and configured to facilitate communications between the device and an unsecured network;
  a plurality of logical local ports provided at the housing and configured to implement a plurality of disparate communication protocols for effecting connectivity between the device and the plurality of PPCs;
  a processor provided at the housing and coupled to the logical network port and the plurality of logical local ports; and
  memory provided at the housing and coupled to the processor, the memory storing life critical network (LCN) software comprising program instructions which, when executed by the processor, cause the processor to detect presence of entities that come into proximity with the communications device, determine whether or not the entities requesting a network connection via the device are PPCs, authenticate only PPCs to the CA to establish a secured connection between each PPC and the CA, initiate interrogation of each PPC in response to the PPC coming into proximity with the communications device, facilitate communication between the PPCs and the CA via the logical local ports, the logical network port, and the unsecured network upon successful PPC authentication, and transfer PPC data to the CA, at least a portion of the PPC data comprising PIMD data.

2. The device of claim 1, wherein program instructions of the LCN software, when executed by the processor, provides a connection mapping and authentication to the CA only for entities that are determined by the processor to be PPCs.

3. The device of claim 1, wherein the plurality of logical local ports comprises a plurality of wireless access ports.

4. The device of claim 3, wherein the plurality of logical local ports comprises at least one wired access port.

5. The device of claim 1, wherein program instructions of the LCN software, when executed by the processor, cause the processor to transmit a request to each PPC to interrogate their respective PIMDs.

6. The device of claim 1, wherein the device defines a hub, a switch, or a router.

7. The device of claim 6, wherein the memory of the hub, switch, or router stores the LCN software and general Internet access software comprising program instructions which, when executed by the processor, cause the processor to facilitate communication between non-PPC entities and the Internet via the logical local ports, the logical network port, and the unsecured network.

8. The device of claim 1, wherein the device defines a general purpose communications device that is transformed to function as a special purpose communications device upon receiving and storing the LCN software in the memory.

9. The device of claim 1, wherein the device defines or is integral to a PIMD programmer.

10. The device of claim 9, wherein program instructions of the LCN software, when executed by the processor, cause the processor to automatically interrogate PPCs in response to the PPCs coming into proximity with the programmer, request the PPCs to interrogate their respective PIMDs, transfer data from the PPCs to the memory of the programmer, authenticate the programmer with the CA, and transfer the PPC data from the memory of the programmer to the CA via the logical local ports, the logical network port, and the unsecured network upon successful programmer authentication, at least a portion of the PPC data comprising PIMD data.

11. The device of claim 9, wherein the data transferred from the PPCs to the memory of the programmer are encrypted or secured in a manner that prevents the programmer from deciphering some or all of the PPC data.

12. The device of claim 9, wherein program instructions of the LCN software, when executed by the processor, cause the processor to generate a unique session ID code for each PPC with which the programmer communicates, transmit the session ID code to each respective PPC, append the session ID code to PPC data prior to encrypting or securing the PPC data by each respective PPC, authenticate the programmer to the CA via the unsecured network, transmit the secured PPC data to the CA upon successful programmer authentication, and receive, from the CA, unencrypted PPC data in a format that allows for displaying or printing by the programmer.

13. The device of claim 1, wherein the memory further stores general Internet access software comprising program instructions which, when executed by the processor, cause the processor to facilitate communication between non-PPC entities and the Internet via the logical local ports, the logical network port, and the unsecured network.

14. A method for effecting secured communications between a plurality of portable patient communicators (PPC) and a central authority (CA) using a communications device via an unsecured network, each of the plurality of PPCs configured to effect connectivity with a patient implantable medical device (PIMD), the method comprising:

detecting, using a plurality of disparate communication protocols implemented by the communications device, presence of each of a plurality of entities requesting a network connection;
determining whether or not each of the entities is a PPC;
establishing, only for the entities determined to be PPCs, a connection to the CA via the unsecured network using the disparate communication protocols implemented by the communications device;
authenticating only the PPCs to the CA via the communications device and the unsecured network;
facilitating communication of PPC data between the PPCs and the CA via the communications device and the unsecured network upon successful PPC authentication, the PPC data comprising at least some PIMD data acquired from PIMDs by their respective PPCs; interrogating PPCs coming into proximity with the communications device;
requesting each of the PPCs interrogate their respective PIMDs;
transferring data from the PPCs to the memory of the communications device;
authenticating the communications device with the CA; and
transferring the PPC data from the memory of the communications device to the CA via the logical local ports, the logical network port, and the unsecured network upon successful communications device authentication, at least a portion of the PPC data comprising PIMD data.

15. The method of claim 14, further comprising establishing, for at least some of the entities determined to be PPCs, a wireless connection to the CA using disparate wireless communication protocols implemented by the communications device and the unsecured network.

16. The method of claim 14, wherein the device defines a hub, a switch, or a router.

17. The method of claim 14, wherein the device defines an implantable medical device programmer, and the method comprises:
generating, by the programmer when interrogating each of the PPCs, a unique session ID code and appending the session ID code to the PIMD data prior to encrypting or securing the PPC data;
and
receiving, from the CA, unencrypted PPC data in a format that allows for displaying or printing by the programmer.

18. A non-transitory computer-readable medium having instructions stored thereon which are executable by a data processing arrangement disposed in a communications device configured to be coupled to an unsecured network, wherein the instructions, when executed, causes the communications device to perform the steps comprising:
detecting, using a plurality of disparate communication protocols implemented by the communications device, presence of each of a plurality of entities requesting a network connection;
determining whether or not each of the entities is a portable patient communicator (PPC), each of the PPCs configured to effect connectivity with a patient implantable medical device (PIMD);
establishing, only for the entities determined to be PPCs, a connection to the CA via the unsecured network using the disparate communication protocols implementable by the communications device;
authenticating only the PPCs to the CA via the communications device and the unsecured network;

interrogating PPCs coming into proximity with the communications device;
facilitating communication of PPC data between the PPCs and the CA via the communications device and the unsecured network upon successful PPC authentication, the PPC data comprising at least some PIMD data acquired from PIMDs by their respective PPCs; and
facilitating communication between non-PPC entities and the Internet via the logical local ports, the logical network port, and the unsecured network.

* * * * *